(12) United States Patent
Wakai

(10) Patent No.: US 9,506,054 B2
(45) Date of Patent: Nov. 29, 2016

(54) METHOD FOR ACQUIRING A HEAT-STABLE ANTIBODY-DISPLAYED PHAGE

(71) Applicant: PANASONIC CORPORATION, Osaka (JP)

(72) Inventor: Junko Wakai, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 422 days.

(21) Appl. No.: 14/151,508

(22) Filed: Jan. 9, 2014

(65) Prior Publication Data

US 2014/0128569 A1    May 8, 2014

Related U.S. Application Data

(63) Continuation of application No. PCT/JP2012/004306, filed on Jul. 3, 2012.

(30) Foreign Application Priority Data

May 14, 2012 (JP) ................................. 2012-110220

(51) Int. Cl.
*C12N 15/10* (2006.01)
*C07K 14/00* (2006.01)
(Continued)

(52) U.S. Cl.
CPC ............ *C12N 15/1037* (2013.01); *C07K 14/00* (2013.01); *C07K 14/001* (2013.01); *C07K 14/47* (2013.01); *C07K 14/4716* (2013.01); *C07K 7/08* (2013.01)

(58) Field of Classification Search
CPC  C12N 15/1037; C07K 14/00; C07K 14/001; C07K 14/4716; C07K 7/08
See application file for complete search history.

(56) References Cited

U.S. PATENT DOCUMENTS

2002/0177170 A1*  11/2002  Luo ......................... C40B 50/02
                                                           435/7.1
2009/0005257 A1    1/2009  Jespers et al.

FOREIGN PATENT DOCUMENTS

JP    2007535484 A    12/2007
JP    2009280616 A    12/2009
(Continued)

OTHER PUBLICATIONS

Notification of Transmittal of Translation of the International Preliminary Report on Patentability (Chapter 1) dated Nov. 27, 2014 issued in International Application No. PCT/JP2012/004306.
(Continued)

*Primary Examiner* — Jeremy C Flinders
(74) *Attorney, Agent, or Firm* — McDermott Will & Emery LLP

(57) ABSTRACT

Using a biopanning method, a heat-stable antibody-displayed phage is acquired. More particularly, first, an antibody-displayed phage library aqueous solution containing plural types of antibody-displayed phages is supplied to a support comprising a polypeptide on the surface thereof, so as to bind the plural types of the antibody-displayed phages to the polypeptide specifically. Next, the support is heated to the temperature of not less than 37 degrees Celsius and not more than 70 degrees Celsius, so as to release a portion of the antibody-displayed phages from the support and so as to leave the other antibody-displayed phages on the support selectively. Finally, the other antibody-displayed phages which has been left on the support selectively in the previous step is collected to obtain the heat-stable antibody-displayed phage.

7 Claims, 6 Drawing Sheets

(51) Int. Cl.
   C07K 14/47       (2006.01)
   C07K 7/08        (2006.01)

(56)           References Cited

FOREIGN PATENT DOCUMENTS

WO        96-40749   A1    12/1996
WO        98-56900   A1    12/1998
WO        03-099999  A2    12/2003
WO     2004-101790   A1    11/2004

OTHER PUBLICATIONS

Jespers, L., et al.: "Aggregation-resistant domain antibodies selected on phage by heat denaturation", Nature Biotechnology, Sep. 2004, vol. 22, No. 9, pp. 1161-1165.

Olichon, A., et al.: "Heating as a rapid purification method for recovering correctly-folded thermotolerant VH and VHH domains", BMC Biotechnology, 2007, vol. 7, pp. 1-8.

Christ, D., et al.: "Repertoires of aggregation-resistant human antibody domains", Protein Engineering, Design & Selection, 2007, vol. 20, No. 8, pp. 413-416.

Okamoto, T., et al.: "Optimal construction of non-immune scFv phage display libraries from mouse bone marrow and spleen established to select soecific scFvs efficiently binding to antigen", Biochemical and Biophysical Research Communications, 2004, vol. 323, pp. 583-591.

Qi, H., et al.: "Phagemid Vectors for Phage Display: Properties, Characteristics and Construction", Journal of Molecular Biology, 2012, vol. 417, pp. 129-143.

Winter, G., et al.: "Making Antibodies by Phage Display Technology", Annual Review of Immunology, 1994, vol. 12, pp. 433-455.

International Search Report issued in PCT/JP2012/004306, dated Oct. 9, 2012.

* cited by examiner

SEQUENCE LISTING

<160> NUMBER OF SEQ ID NOS: 69

<210> SEQ ID NO 1
<211> LENGTH: 45
<212> TYPE: PRT
<213> ORGANISM: Artificial
<220> FEATURE:
<223> OTHER INFORMATION: Heat-stable peptide

<400> SEQUENCE: 1

Cys Ala Pro Ala Pro Ile Arg Arg Ser Ser Asn Tyr Arg Ala Tyr
1               5                   10                  15

Ala Thr Glu Pro His Ala Lys Lys Lys Ser Lys Ile Ser Ala Ser Arg
            20                  25                  30

Lys Leu Gln Leu Lys Thr Leu Leu Leu Gln Ile Ala Lys
        35                  40                  45

<210> SEQ ID NO 2
<211> LENGTH: 50
<212> TYPE: DNA
<213> ORGANISM: Artificial
<220> FEATURE:
<223> OTHER INFORMATION: primer

<400> SEQUENCE: 2
cctttctatg cggcccagcc ggccatggcc gayattgtwc tcwcccartc            50

<210> SEQ ID NO 3
<211> LENGTH: 50
<212> TYPE: DNA
<213> ORGANISM: Artificial
<220> FEATURE:
<223> OTHER INFORMATION: primer

<400> SEQUENCE: 3
cctttctatg cggcccagcc ggccatggcc gayattstgm tsacycagtc            50

<210> SEQ ID NO 4
<211> LENGTH: 50
<212> TYPE: DNA
<213> ORGANISM: Artificial
<220> FEATURE:
<223> OTHER INFORMATION: primer

<400> SEQUENCE: 4
cctttctatg cggcccagcc ggccatggcc gayattgtgm tmactcagtc            50

<210> SEQ ID NO 5
<211> LENGTH: 50
<212> TYPE: DNA
<213> ORGANISM: Artificial
<220> FEATURE:
<223> OTHER INFORMATION: primer

<400> SEQUENCE: 5
cctttctatg cggcccagcc ggccatggcc gayattgtgh trwcacagtc            50

<210> SEQ ID NO 6
<211> LENGTH: 50
<212> TYPE: DNA
<213> ORGANISM: Artificial
<220> FEATURE:
<223> OTHER INFORMATION: primer

<400> SEQUENCE: 6

```
cctttctatg cggcccagcc ggccatggcc gayattgtra tgacmcagtc                50
```

<210> SEQ ID NO 7
<211> LENGTH: 50
<212> TYPE: DNA
<213> ORGANISM: Artificial
<220> FEATURE:
<223> OTHER INFORMATION: primer

<400> SEQUENCE: 7

```
cctttctatg cggcccagcc ggccatggcc gayattmaga tramccagtc                50
```

<210> SEQ ID NO 8
<211> LENGTH: 50
<212> TYPE: DNA
<213> ORGANISM: Artificial
<220> FEATURE:
<223> OTHER INFORMATION: primer

<400> SEQUENCE: 8

```
cctttctatg cggcccagcc ggccatggcc gayattcaga tgaydcagtc                50
```

<210> SEQ ID NO 9
<211> LENGTH: 50
<212> TYPE: DNA
<213> ORGANISM: Artificial
<220> FEATURE:
<223> OTHER INFORMATION: primer

<400> SEQUENCE: 9

```
cctttctatg cggcccagcc ggccatggcc gayattttgc tgactcagtc                50
```

<210> SEQ ID NO 10
<211> LENGTH: 50
<212> TYPE: DNA
<213> ORGANISM: Artificial
<220> FEATURE:
<223> OTHER INFORMATION: primer

<400> SEQUENCE: 10

```
cctttctatg cggcccagcc ggccatggcc gayattgttc tcawccagtc                50
```

<210> SEQ ID NO 11
<211> LENGTH: 50
<212> TYPE: DNA
<213> ORGANISM: Artificial
<220> FEATURE:
<223> OTHER INFORMATION: primer

<400> SEQUENCE: 11

```
cctttctatg cggcccagcc ggccatggcc gayattgwgc tsacccaatc                50
```

<210> SEQ ID NO 12
<211> LENGTH: 50
<212> TYPE: DNA
<213> ORGANISM: Artificial
<220> FEATURE:
<223> OTHER INFORMATION: primer

<400> SEQUENCE: 12

```
cctttctatg cggcccagcc ggccatggcc gayattstra tgacccartc                50
```

<210> SEQ ID NO 13
<211> LENGTH: 50
<212> TYPE: DNA
<213> ORGANISM: Artificial

```
<220> FEATURE:
<223> OTHER INFORMATION: primer

<400> SEQUENCE: 13
cctttctatg cggcccagcc ggccatggcc gayrttktga tgacccavac      50

<210> SEQ ID NO 14
<211> LENGTH: 50
<212> TYPE: DNA
<213> ORGANISM: Artificial
<220> FEATURE:
<223> OTHER INFORMATION: primer

<400> SEQUENCE: 14
cctttctatg cggcccagcc ggccatggcc gayatycaga tgacacagac      50

<210> SEQ ID NO 15
<211> LENGTH: 50
<212> TYPE: DNA
<213> ORGANISM: Artificial
<220> FEATURE:
<223> OTHER INFORMATION: primer

<400> SEQUENCE: 15
cctttctatg cggcccagcc ggccatggcc gayattgtga tgacacaacc      50

<210> SEQ ID NO 16
<211> LENGTH: 50
<212> TYPE: DNA
<213> ORGANISM: Artificial
<220> FEATURE:
<223> OTHER INFORMATION: primer

<400> SEQUENCE: 16
cctttctatg cggcccagcc ggccatggcc gayatccagc tgactcagcc      50

<210> SEQ ID NO 17
<211> LENGTH: 50
<212> TYPE: DNA
<213> ORGANISM: Artificial
<220> FEATURE:
<223> OTHER INFORMATION: primer

<400> SEQUENCE: 17
cctttctatg cggcccagcc ggccatggcc gayattgtga tgacbcagkc      50

<210> SEQ ID NO 18
<211> LENGTH: 50
<212> TYPE: DNA
<213> ORGANISM: Artificial
<220> FEATURE:
<223> OTHER INFORMATION: primer

<400> SEQUENCE: 18
cctttctatg cggcccagcc ggccatggcc gayattgtga taacycagga      50

<210> SEQ ID NO 19
<211> LENGTH: 50
<212> TYPE: DNA
<213> ORGANISM: Artificial
<220> FEATURE:
<223> OTHER INFORMATION: primer

<400> SEQUENCE: 19
cctttctatg cggcccagcc ggccatggcc gayattgtga tgacccagwt      50
```

<210> SEQ ID NO 20
<211> LENGTH: 50
<212> TYPE: DNA
<213> ORGANISM: Artificial
<220> FEATURE:
<223> OTHER INFORMATION: primer

<400> SEQUENCE: 20
cctttctatg cggcccagcc ggccatggcc gaygtgstgm tsacycagtc          50

<210> SEQ ID NO 21
<211> LENGTH: 52
<212> TYPE: DNA
<213> ORGANISM: Artificial
<220> FEATURE:
<223> OTHER INFORMATION: primer

<400> SEQUENCE: 21
cctttctatg cggcccagcc ggccatggcc gaygctgttg tactcaggaa tc       52

<210> SEQ ID NO 22
<211> LENGTH: 50
<212> TYPE: DNA
<213> ORGANISM: Artificial
<220> FEATURE:
<223> OTHER INFORMATION: primer

<400> SEQUENCE: 22
cctttctatg cggcccagcc ggccatggcc gayattgtdh tvwchcagtc          50

<210> SEQ ID NO 23
<211> LENGTH: 53
<212> TYPE: DNA
<213> ORGANISM: Artificial
<220> FEATURE:
<223> OTHER INFORMATION: primer

<400> SEQUENCE: 23
agcggcggcg gcggctctgg tggtggtgga tccgakgtrm agcttcagga gyc      53

<210> SEQ ID NO 24
<211> LENGTH: 53
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (39)..(39)
<223> OTHER INFORMATION: n stands for any base

<400> SEQUENCE: 24
agcggcggcg gcggctctgg tggtggtgga tccgaggtnc agctbcagca gtc      53

<210> SEQ ID NO 25
<211> LENGTH: 53
<212> TYPE: DNA
<213> ORGANISM: Artificial
<220> FEATURE:
<223> OTHER INFORMATION: primer

<400> SEQUENCE: 25
agcggcggcg gcggctctgg tggtggtgga tcccaggtgc agctgaagsa stc      53

<210> SEQ ID NO 26
<211> LENGTH: 53

```
<212> TYPE: DNA
<213> ORGANISM: Artificial
<220> FEATURE:
<223> OTHER INFORMATION: primer

<400> SEQUENCE: 26
agcggcggcg gcggctctgg tggtggtgga tcccagstbc agctgcagca gtc      53

<210> SEQ ID NO 27
<211> LENGTH: 53
<212> TYPE: DNA
<213> ORGANISM: Artificial
<220> FEATURE:
<223> OTHER INFORMATION: primer

<400> SEQUENCE: 27
agcggcggcg gcggctctgg tggtggtgga tccgaggtyc agctycagca gtc      53

<210> SEQ ID NO 28
<211> LENGTH: 53
<212> TYPE: DNA
<213> ORGANISM: Artificial
<220> FEATURE:
<223> OTHER INFORMATION: primer

<400> SEQUENCE: 28
agcggcggcg gcggctctgg tggtggtgga tccgargtcc arctgcaaca rtc      53

<210> SEQ ID NO 29
<211> LENGTH: 53
<212> TYPE: DNA
<213> ORGANISM: Artificial
<220> FEATURE:
<223> OTHER INFORMATION: primer

<400> SEQUENCE: 29
agcggcggcg gcggctctgg tggtggtgga tcccaggtyc agctbcagca rtc      53

<210> SEQ ID NO 30
<211> LENGTH: 53
<212> TYPE: DNA
<213> ORGANISM: Artificial
<220> FEATURE:
<223> OTHER INFORMATION: primer

<400> SEQUENCE: 30
agcggcggcg gcggctctgg tggtggtgga tcccaggtyc arctkcagca gtc      53

<210> SEQ ID NO 31
<211> LENGTH: 53
<212> TYPE: DNA
<213> ORGANISM: Artificial
<220> FEATURE:
<223> OTHER INFORMATION: primer

<400> SEQUENCE: 31
agcggcggcg gcggctctgg tggtggtgga tcccaggtcc acgtgaagca gtc      53

<210> SEQ ID NO 32
<211> LENGTH: 53
<212> TYPE: DNA
<213> ORGANISM: Artificial
<220> FEATURE:
<223> OTHER INFORMATION: primer

<400> SEQUENCE: 32
```

```
agcggcggcg gcggctctgg tggtggtgga tccgaggtga asstggtgga rtc    53
```

<210> SEQ ID NO 33
<211> LENGTH: 53
<212> TYPE: DNA
<213> ORGANISM: Artificial
<220> FEATURE:
<223> OTHER INFORMATION: primer

<400> SEQUENCE: 33

```
agcggcggcg gcggctctgg tggtggtgga tccgavgtga wgytggtgga gtc    53
```

<210> SEQ ID NO 34
<211> LENGTH: 53
<212> TYPE: DNA
<213> ORGANISM: Artificial
<220> FEATURE:
<223> OTHER INFORMATION: primer

<400> SEQUENCE: 34

```
agcggcggcg gcggctctgg tggtggtgga tccgaggtga aggtcatcga gtc    53
```

<210> SEQ ID NO 35
<211> LENGTH: 53
<212> TYPE: DNA
<213> ORGANISM: Artificial
<220> FEATURE:
<223> OTHER INFORMATION: primer

<400> SEQUENCE: 35

```
agcggcggcg gcggctctgg tggtggtgga tccsaggtgc agskggtgga gtc    53
```

<210> SEQ ID NO 36
<211> LENGTH: 53
<212> TYPE: DNA
<213> ORGANISM: Artificial
<220> FEATURE:
<223> OTHER INFORMATION: primer

<400> SEQUENCE: 36

```
agcggcggcg gcggctctgg tggtggtgga tccgakgtgc amctggtgga gtc    53
```

<210> SEQ ID NO 37
<211> LENGTH: 53
<212> TYPE: DNA
<213> ORGANISM: Artificial
<220> FEATURE:
<223> OTHER INFORMATION: primer

<400> SEQUENCE: 37

```
agcggcggcg gcggctctgg tggtggtgga tccgaagtgc avctggtgga gtc    53
```

<210> SEQ ID NO 38
<211> LENGTH: 53
<212> TYPE: DNA
<213> ORGANISM: Artificial
<220> FEATURE:
<223> OTHER INFORMATION: primer

<400> SEQUENCE: 38

```
agcggcggcg gcggctctgg tggtggtgga tccgaggtga agctgatgga rtc    53
```

<210> SEQ ID NO 39
<211> LENGTH: 53
<212> TYPE: DNA
<213> ORGANISM: Artificial

```
<220> FEATURE:
<223> OTHER INFORMATION: primer

<400> SEQUENCE: 39
agcggcggcg gcggctctgg tgtggtgga tccgaggtgc arcttgttga gtc        53

<210> SEQ ID NO 40
<211> LENGTH: 53
<212> TYPE: DNA
<213> ORGANISM: Artificial
<220> FEATURE:
<223> OTHER INFORMATION: primer

<400> SEQUENCE: 40
agcggcggcg gcggctctgg tgtggtgga tccgargtra agcttctcga gtc        53

<210> SEQ ID NO 41
<211> LENGTH: 53
<212> TYPE: DNA
<213> ORGANISM: Artificial
<220> FEATURE:
<223> OTHER INFORMATION: primer

<400> SEQUENCE: 41
agcggcggcg gcggctctgg tgtggtgga tccgaagtga arsttgagga gtc        53

<210> SEQ ID NO 42
<211> LENGTH: 53
<212> TYPE: DNA
<213> ORGANISM: Artificial
<220> FEATURE:
<223> OTHER INFORMATION: primer

<400> SEQUENCE: 42
agcggcggcg gcggctctgg tgtggtgga tccgaagtga tgctggtgga gtc        53

<210> SEQ ID NO 43
<211> LENGTH: 55
<212> TYPE: DNA
<213> ORGANISM: Artificial
<220> FEATURE:
<223> OTHER INFORMATION: primer

<400> SEQUENCE: 43
agcggcggcg gcggctctgg tgtggtgga tcccaggtta ctctraaagw gtstg      55

<210> SEQ ID NO 44
<211> LENGTH: 53
<212> TYPE: DNA
<213> ORGANISM: Artificial
<220> FEATURE:
<223> OTHER INFORMATION: primer

<400> SEQUENCE: 44
agcggcggcg gcggctctgg tgtggtgga tcccaggtcc aaytvcagca rcc        53

<210> SEQ ID NO 45
<211> LENGTH: 53
<212> TYPE: DNA
<213> ORGANISM: Artificial
<220> FEATURE:
<223> OTHER INFORMATION: primer

<400> SEQUENCE: 45
agcggcggcg gcggctctgg tgtggtgga tccgatgtga acttggaagt gtc        53
```

<210> SEQ ID NO 46
<211> LENGTH: 53
<212> TYPE: DNA
<213> ORGANISM: Artificial
<220> FEATURE:
<223> OTHER INFORMATION: primer

<400> SEQUENCE: 46
accagagccg ccgccgccgc taccaccacc ccccgtttg atttccarct tkg    53

<210> SEQ ID NO 47
<211> LENGTH: 53
<212> TYPE: DNA
<213> ORGANISM: Artificial
<220> FEATURE:
<223> OTHER INFORMATION: primer

<400> SEQUENCE: 47
accagagccg ccgccgccgc taccaccacc ccccgtttt atttccagct tgg    53

<210> SEQ ID NO 48
<211> LENGTH: 53
<212> TYPE: DNA
<213> ORGANISM: Artificial
<220> FEATURE:
<223> OTHER INFORMATION: primer

<400> SEQUENCE: 48
accagagccg ccgccgccgc taccaccacc ccccgttts agctccagct tgg    53

<210> SEQ ID NO 49
<211> LENGTH: 53
<212> TYPE: DNA
<213> ORGANISM: Artificial
<220> FEATURE:
<223> OTHER INFORMATION: primer

<400> SEQUENCE: 49
accagagccg ccgccgccgc taccaccacc ccccgttyw atttccaact twg    53

<210> SEQ ID NO 50
<211> LENGTH: 53
<212> TYPE: DNA
<213> ORGANISM: Artificial
<220> FEATURE:
<223> OTHER INFORMATION: primer

<400> SEQUENCE: 50
accagagccg ccgccgccgc taccaccacc ccccctagg acagtcagtt tgg    53

<210> SEQ ID NO 51
<211> LENGTH: 45
<212> TYPE: DNA
<213> ORGANISM: Artificial
<220> FEATURE:
<223> OTHER INFORMATION: primer

<400> SEQUENCE: 51
cggcaccggc gcacctgcgg ccgcygagga aacggtgacc gtggt    45

<210> SEQ ID NO 52
<211> LENGTH: 45
<212> TYPE: DNA
<213> ORGANISM: Artificial
<220> FEATURE:
<223> OTHER INFORMATION: primer

<400> SEQUENCE: 52
cggcaccggc gcacctgcgg ccgcygagga gactgtgaga gtggt                45

<210> SEQ ID NO 53
<211> LENGTH: 45
<212> TYPE: DNA
<213> ORGANISM: Artificial
<220> FEATURE:
<223> OTHER INFORMATION: primer

<400> SEQUENCE: 53
cggcaccggc gcacctgcgg ccgcygagga gacggtgact gagrt                45

<210> SEQ ID NO 54
<211> LENGTH: 45
<212> TYPE: DNA
<213> ORGANISM: Artificial
<220> FEATURE:
<223> OTHER INFORMATION: primer

<400> SEQUENCE: 54
cggcaccggc gcacctgcgg ccgcygagga agactgtaga gtggt                45

<210> SEQ ID NO 55
<211> LENGTH: 45
<212> TYPE: DNA
<213> ORGANISM: Artificial
<220> FEATURE:
<223> OTHER INFORMATION: primer

<400> SEQUENCE: 55
cggcaccggc gcacctgcgg ccgcygcgga gacastgacc agagt                45

<210> SEQ ID NO 56
<211> LENGTH: 45
<212> TYPE: DNA
<213> ORGANISM: Artificial
<220> FEATURE:
<223> OTHER INFORMATION: primer

<400> SEQUENCE: 56
cggcaccggc gcacctgcgg ccgcygcaga gacastgacc agagt                45

<210> SEQ ID NO 57
<211> LENGTH: 45
<212> TYPE: DNA
<213> ORGANISM: Artificial
<220> FEATURE:
<223> OTHER INFORMATION: Primer

<400> SEQUENCE: 57
ttaaaggccc agccggccat ggctgacgtg gtgctcactc agtct                45

<210> SEQ ID NO 58
<211> LENGTH: 18
<212> TYPE: DNA
<213> ORGANISM: Artificial
<220> FEATURE:
<223> OTHER INFORMATION: Primer

<400> SEQUENCE: 58
ctcgagtgcg gccgctga                                              18

<210> SEQ ID NO 59

```
<211> LENGTH: 15
<212> TYPE: PRT
<213> ORGANISM: Artificial
<220> FEATURE:
<223> OTHER INFORMATION: Linker

<400> SEQUENCE: 59

Gly Gly Gly Gly Ser Gly Gly Gly Gly Ser Gly Gly Gly Gly Ser
1               5                   10                  15

<210> SEQ ID NO 60
<211> LENGTH: 339
<212> TYPE: DNA
<213> ORGANISM: Artificial
<220> FEATURE:
<223> OTHER INFORMATION: base sequence coding for the light chain
      variable region

<400> SEQUENCE: 60
gacgtggtga tcactcagtc tccactcact tgtcggtta ccattggaca accagcctcc      60
atctcttgca agtcaagtca gagcctctta gatagtgatg aaagacata tttgaattgg    120 ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttcct    300
cagacgttcg gtggaggcac caagctggaa ataaaacgg                           339

<210> SEQ ID NO 61
<211> LENGTH: 45
<212> TYPE: DNA
<213> ORGANISM: Artificial
<220> FEATURE:
<223> OTHER INFORMATION: base sequence coding for the linker

<400> SEQUENCE: 61
ggtggtggtg gtagcggcgg cggcggctct ggtggtggtg gatcc                     45

<210> SEQ ID NO 62
<211> LENGTH: 345
<212> TYPE: DNA
<213> ORGANISM: Artificial
<220> FEATURE:
<223> OTHER INFORMATION: base sequence coding for the heavy chain
      variable region

<400> SEQUENCE: 62
gaggttcagc ttcagcagtc tggggcggag cttgcgaggt caggggcctc agtcaagttg      60
tcctgcacag cttctggctt caacattaaa gactactata tgaactggat gaggcagagg    120
cctgaacagg gcctggagtg gattggatgg attgatcctg cgaatggtga tactgcatat    180
gccccgaggt tccaggtcaa ggccactatg actgcagaca aatcctccaa cacagcctac    240
ctgcagctca aagcctgac atctgaggac actgccgtct attactgtaa tgctgatctc    300
cctatggacc agtggggtca aggaaccacg gtcaccgttt cctcg                    345

<210> SEQ ID NO 63
<211> LENGTH: 113
<212> TYPE: PRT
<213> ORGANISM: Artificial
<220> FEATURE:
<223> OTHER INFORMATION: light chain variable region

<400> SEQUENCE: 63
```

-continued

Asp Val Val Ile Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

Arg

<210> SEQ ID NO 64
<211> LENGTH: 15
<212> TYPE: PRT
<213> ORGANISM: Artificial
<220> FEATURE:
<223> OTHER INFORMATION: Linker

<400> SEQUENCE: 64

Gly Gly Gly Gly Ser Gly Gly Gly Gly Ser Gly Gly Gly Gly Ser
1               5                   10                  15

<210> SEQ ID NO 65
<211> LENGTH: 115
<212> TYPE: PRT
<213> ORGANISM: Artificial
<220> FEATURE:
<223> OTHER INFORMATION: Heavy chain variable region

<400> SEQUENCE: 65

Glu Val Gln Leu Gln Gln Ser Gly Ala Glu Leu Ala Arg Ser Gly Ala
1               5                   10                  15

Ser Val Lys Leu Ser Cys Thr Ala Ser Gly Phe Asn Ile Lys Asp Tyr
            20                  25                  30

Tyr Met Asn Trp Met Arg Gln Arg Pro Glu Gln Gly Leu Glu Trp Ile
        35                  40                  45

Gly Trp Ile Asp Pro Ala Asn Gly Asp Thr Ala Tyr Ala Pro Arg Phe
    50                  55                  60

Gln Val Lys Ala Thr Met Thr Ala Asp Lys Ser Ser Asn Thr Ala Tyr
65                  70                  75                  80

Leu Gln Leu Arg Ser Leu Thr Ser Glu Asp Thr Ala Val Tyr Tyr Cys
                85                  90                  95

Asn Ala Asp Leu Pro Met Asp Gln Trp Gly Gln Gly Thr Thr Val Thr
            100                 105                 110

Val Ser Ser
        115

<210> SEQ ID NO 66
<211> LENGTH: 729
<212> TYPE: DNA
<213> ORGANISM: Artificial
<220> FEATURE:
<223> OTHER INFORMATION: A2 gene sequence

<400> SEQUENCE: 66

```
gacgtggtgc tcactcagtc tccactcact ttgtcggtta ccattggaca accagcctcc    60
atctcttgca agtcaagtca gagcctctta gatagtgatg aaagacata tttgaattgg    120 ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttcct    300
ctcacgttcg gtgctgggac aaagttggaa attaaacggg gtggtggtgg tagcggcggc    360
ggcggctctg gtggtggtgg atcccagctg cagctgcagc agtctggggc agagcttgtg    420
aggtcagggg cctcagtcaa gttgtcctgc acagcttctg gcttcaacat taaagactac    480
tatatgaact gggtgaagca gaggcctgaa cagggcctgg agtggattgg atggattgat    540
cctgcgaatg gtgatactgc atatgccccg aggttccagg tcaaggccac tatgactgca    600
gacaaatcct ccaacacagc ctacctgcag ctcagcagcc tgacatctga ggacactgcc    660
gtctattact gtaatgctga tctccctatg gaccagtggg gtcaaggaac ctcagtcacc    720
gtctcctca                                                            729
```

<210> SEQ ID NO 67
<211> LENGTH: 339
<212> TYPE: DNA
<213> ORGANISM: Artificial
<220> FEATURE:
<223> OTHER INFORMATION: base sequence coding for the light chain
      variable region

<400> SEQUENCE: 67

```
gacgtggtgc tcactcagtc tccactcact ttgtcggtta ccattggaca accagcctcc    60
atctcttgca agtcaagtca gagcctctta gatagtgatg aaagacata tttgaattgg    120 ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttcct    300
ctcacgttcg gtgctgggac aaagttggaa attaaacgg                           339
```

<210> SEQ ID NO 68
<211> LENGTH: 45
<212> TYPE: DNA
<213> ORGANISM: Artificial
<220> FEATURE:
<223> OTHER INFORMATION: base sequence coding for the linker

<400> SEQUENCE: 68

```
ggtggtggtg gtagcggcgg cggcggctct ggtggtggtg gatcc                     45
```

<210> SEQ ID NO 69
<211> LENGTH: 345
<212> TYPE: DNA
<213> ORGANISM: Artificial
<220> FEATURE:
<223> OTHER INFORMATION: base sequence coding for the heavy chain
      variable region

<400> SEQUENCE: 69

```
cagctgcagc tgcagcagtc tggggcagag cttgtgaggt caggggcctc agtcaagttg    60
tcctgcacag cttctggctt caacattaaa gactactata tgaactgggt gaagcagagg   120
cctgaacagg gcctggagtg gattggatgg attgatcctg cgaatggtga tactgcatat   180
```

-continued

```
gccccgaggt tccaggtcaa ggccactatg actgcagaca aatcctccaa cacagcctac    240
ctgcagctca gcagcctgac atctgaggac actgccgtct attactgtaa tgctgatctc    300
cctatggacc agtggggtca aggaacctca gtcaccgtct cctca                    345
```

METHOD FOR ACQUIRING A HEAT-STABLE ANTIBODY-DISPLAYED PHAGE

CROSS-REFERENCE TO RELATED APPLICATIONS

This is a continuation application of International Application No. PCT/JP2012/004306, with an international filing date of Jul. 3, 2012, which claims priority of Japanese Patent Application No. 2012-110220, filed on May 14, 2012, the entire contents of each of which are incorporated herein by reference.

SEQUENCE LISTING

This application contains a Sequence Listing which has been submitted in ASCII format via EFS-Web and is hereby incorporated by reference in its entirety. Said ASCII copy, created on Jan. 8, 2014, is named SEQUENCE LISTING 043887-0502.txt and is 16,918 bytes in size.

BACKGROUND OF THE INVENTION

Technical Field

The technical field relates to a method for acquiring a heat-stable antibody-displayed phage.

FIG. 1B shows an antibody-displayed phage. The antibody-displayed phage is one kind of phages. The antibody-displayed phage comprises proteins containing a phagemid vector in the inside thereof. In other words, these proteins surround the phagemid vector. The antibody-displayed phage comprises an antibody fragment on the external surface thereof. Two or more antibody fragments may be comprised. The phagemid vector has a gene sequence coding for this antibody fragment.

FIG. 2 shows a method for selecting an antibody-displayed phage having a predetermined property using an antibody phage library which contains plural types of antibody-displayed phages. This method is referred to as "biopanning method".

Each antibody-displayed phage contained in the antibody phage library has a different antibody fragment and a different gene sequence coding for the different antibody fragment.

The biopanning method is briefly described below.

As shown in FIG. 2, first, an aqueous solution containing an antibody phage library is supplied to a support having an antigen corresponding to the predetermined property on the surface thereof. The Antibody-displayed phage having the predetermined property is specifically bound to the antigen. However, the antibody-displayed phage which does not have the predetermined property is removed by washing.

After the antibody-displayed phage which has been specifically bound to the support is collected, the collected antibody-displayed phage is amplified. After the amplification, the antibody-displayed phage is supplied again to the antibody having the antibody on the surface thereof, if necessary.

This procedure is repeated. In this way, the antibody-displayed phage having the predetermined property is collected selectively from the antibody phage library.

CITATION LIST

[Patent Literature 1]
Japanese Patent Laid-Open Publication No. 2009-280616 bulletin (particularly, paragraph 0040) Family: WO96/40749 (Page 15)

[Patent Literature 2]
WO 2003/099999 (particularly, page 160, line 33 to page 162, line 31, more particularly, page 162, line 8 to 9)

SUMMARY

One non-limiting and exemplary embodiment provides a novel method for acquiring a heat-stable antibody-displayed phage.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: A method for acquiring a heat-stable antibody-displayed phage, the method comprising steps of:

(a) supplying an antibody-displayed phage library aqueous solution containing plural types of antibody-displayed phages to a support comprising a polypeptide on the surface thereof, so as to bind the plural types of the antibody-displayed phages to the polypeptide specifically; wherein each antibody-displayed phage comprises proteins containing a phagemid vector in the inside thereof;

each antibody-displayed phage comprises an antibody fragment on the external surface thereof; and the phagemid vector has a gene sequence coding for the antibody fragment;

(b) heating the support to the temperature of not less than 37 degrees Celsius and not more than 70 degrees Celsius, so as to release a portion of the antibody-displayed phages from the support and so as to leave the other antibody-displayed phages on the support selectively; and (c) collecting the other antibody-displayed phages which has been left on the support selectively in the step (b) so as to obtain the heat-stable antibody-displayed phage.

The present disclosure provides a novel method for acquiring a heat-stable antibody-displayed phage.

DETAILED DESCRIPTION

The embodiment according to the present disclosure is described below.

Explanation of the Term

First, the term used in the present specification is described.

Figure 1A:
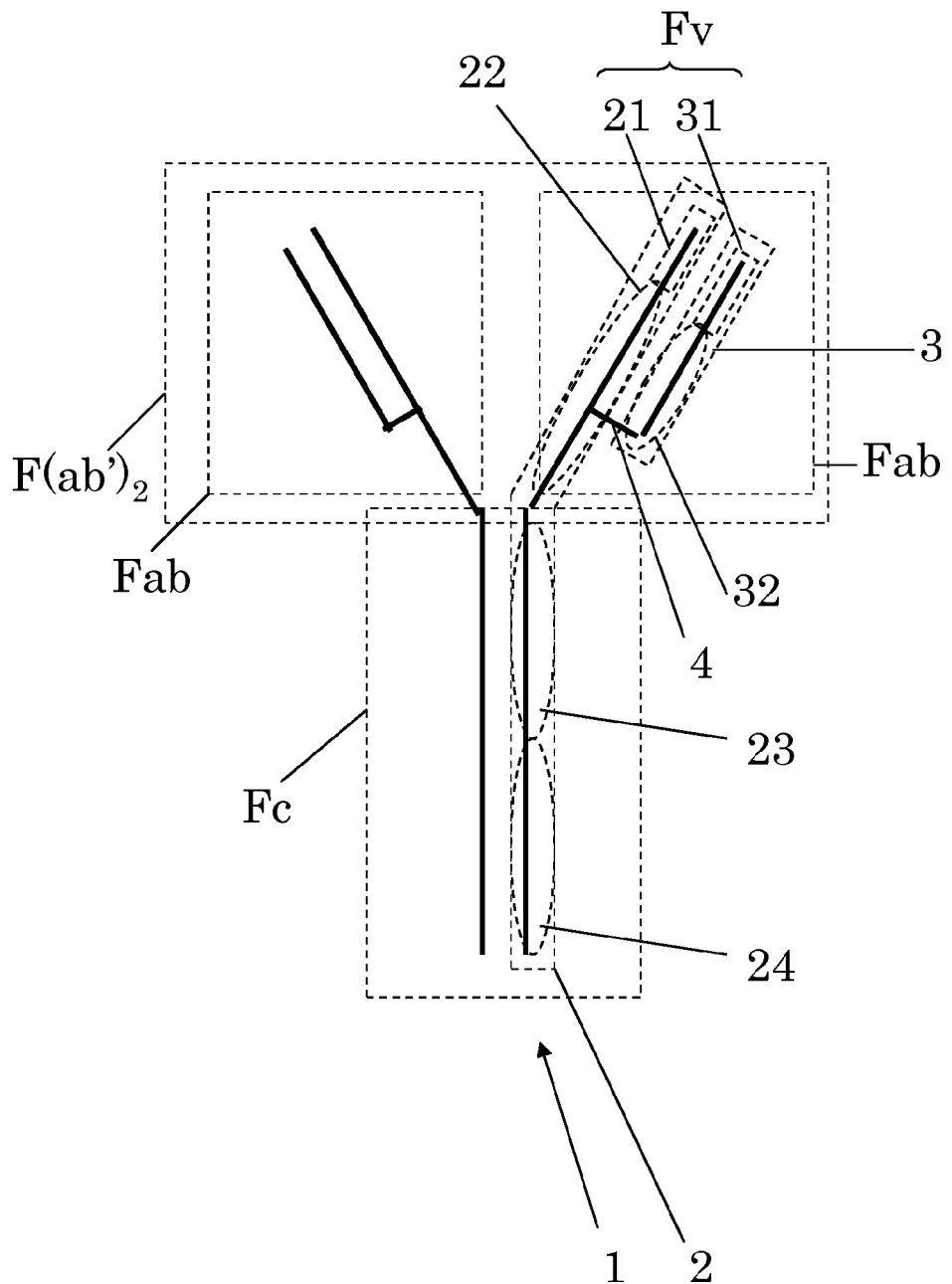
FIG. 1A shows an antibody.

FIG. 1A shows an antibody. As known well, the antibody 1 has a shape of the "Y" letter. The antibody 1 consists of two Fab regions and one Fc region. The antibody 1 consists of two heavy chains 2 and two light chains 3. Each heavy chain 2 consists of a heavy chain constant region 1 (referential sign: 22), a heavy chain constant region 2 (referential sign: 23), and a heavy chain constant region 3 (referential sign: 23), and a heavy chain variable region 21. Each light chain 3 consists of a light chain variable region 31 and a light chain constant region 32.

Each Fab region consists of the one heavy chain variable region 21, the one heavy chain constant region 1 (referential sign: 22), the one light chain variable region 31, and the one light chain constant region 32. The light chain 3 is connected to the heavy chain 2 through a linker 4. The heavy chain 2 has the heavy chain variable region 21 in the end thereof. The light chain 3 has the light chain variable region 31 in the end thereof. An antigen is specifically bound to the antibody 1. In more detail, the antigen is bound specifically to the Fv region, which consists of the heavy chain variable region 21 and the light chain variable region 31.

An example of the antibody fragment is an Fab antibody fragment, an F(ab')$_2$ antibody fragment, or an scFv antibody fragment.

The Fab antibody fragment consists of one Fab region. In other words, the Fab antibody fragment consists of the one light chain variable region 31, the one heavy chain variable region 21, the one light chain constant region 32, the one heavy chain constant region 1 (referential sign: 22), and the linker 4. The light chain constant region 32 is connected to the heavy chain constant region (referential sign: 22) through the linker 4.

The F(ab')$_2$ antibody fragments consists of two Fab regions. As above, each Fab region consists of the one light chain variable region 31, the one heavy chain variable region 21, the one light chain constant region 32, the one heavy chain constant region 1 (referential sign: 22), and the linker 4. These two Fab regions are connected to each other through another liner (not shown). Preferably, one heavy chain constant region 1 (referential sign: 22) is connected to the other heavy chain constant region 1 (referential sign: 22) through the another linker (not shown).

The scFv antibody fragment consists of the light chain variable region 31, the heavy chain variable region 21, and a linker. The light chain variable region 31 is connected to the heavy chain variable region 21 through the linker (not shown).

An example of the linker is a peptide consisting of 5-20 amino acids. More particularly, an example of the linker is the amino acid sequence represented by GGGGSGGGGSGGGGS (SEQ ID NO: 59). Another example of the linker is a disulfide bond (-sulfur atom (S)-sulfur atom (S)—).

(Step (a))

Figure 3:
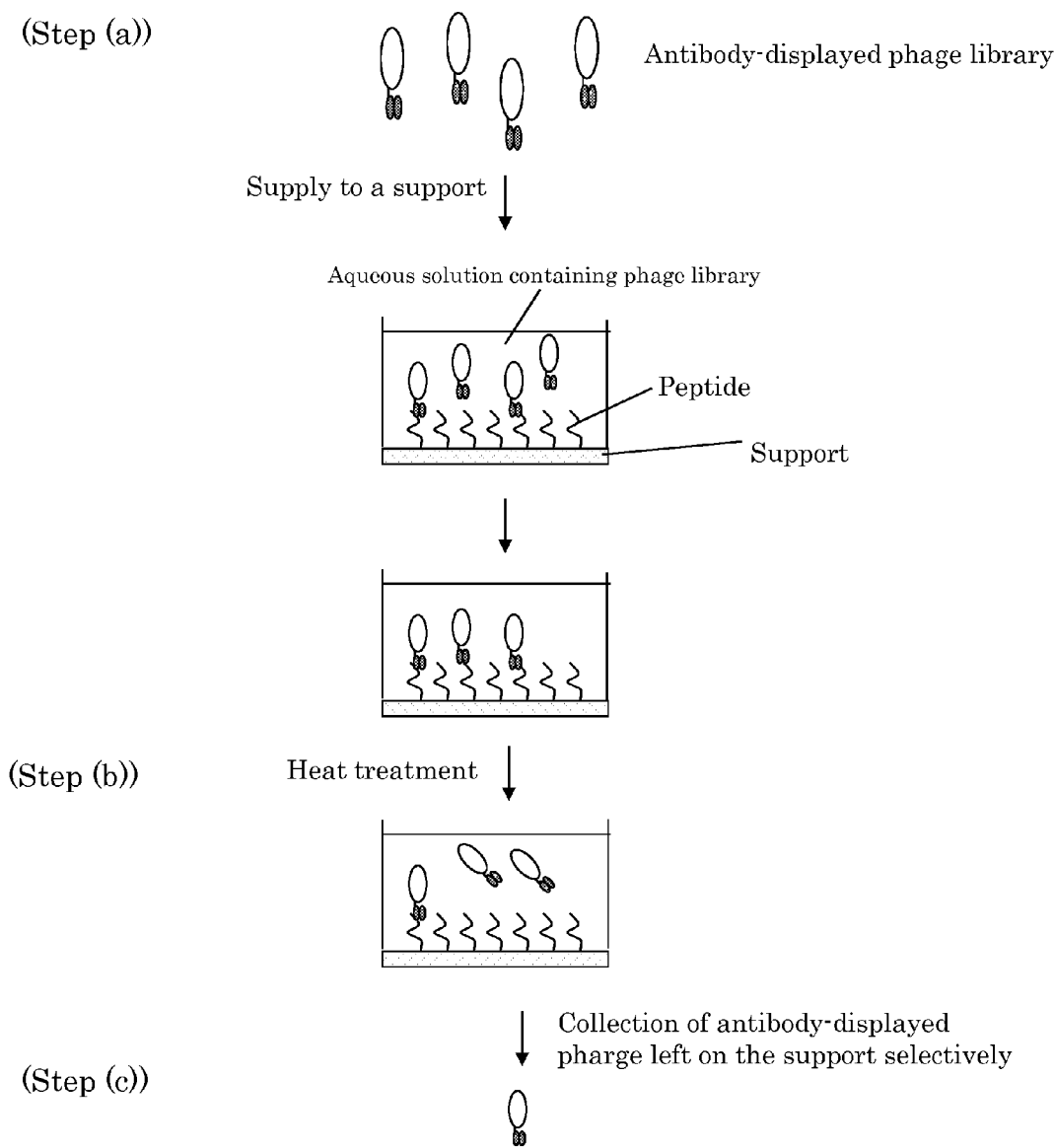
FIG. 3 shows a method for selectively acquiring the heat-stable antibody-displayed phage according to the embodiment.
Figure 4:
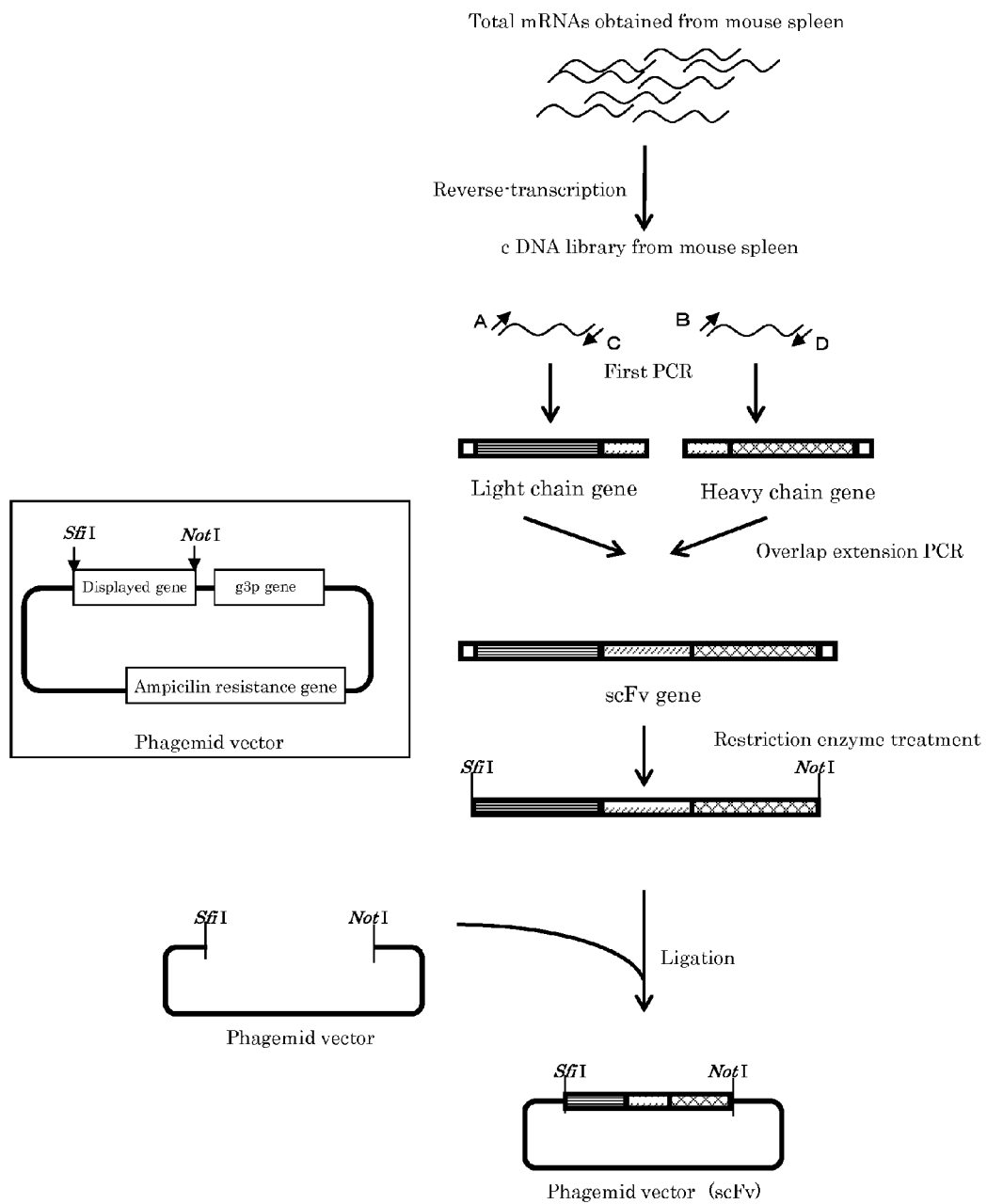
FIG. 4 shows a method for obtaining the phagemid vector according to the example.

FIG. 3 shows a method for selectively acquiring the heat-stable antibody-displayed phage according to the embodiment.

First, in the step (a), an antibody-displayed phage library aqueous solution is prepared. The antibody-displayed phage library aqueous solution contains plural kinds of antibody-displayed phages.

Figure 1B:
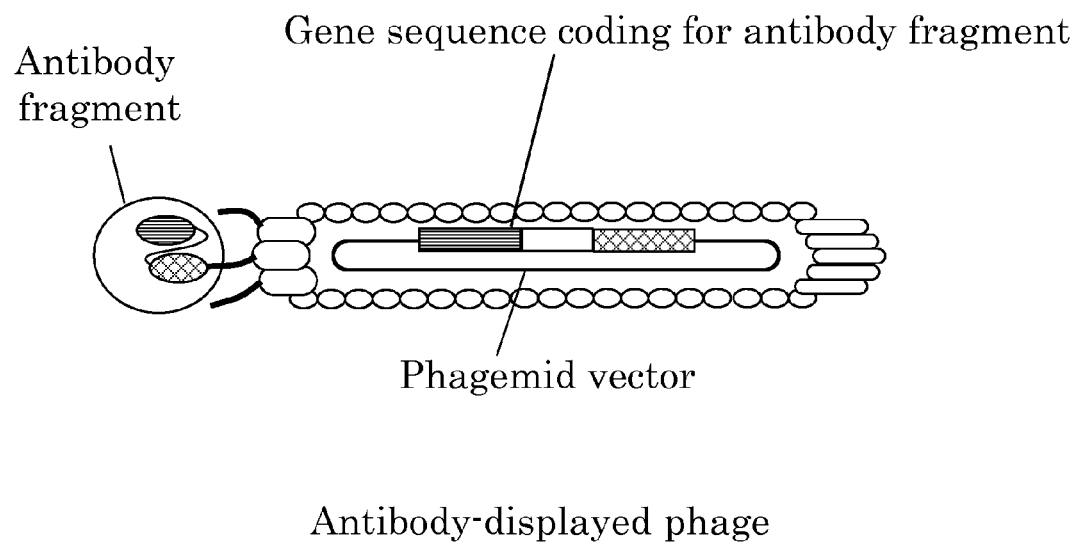
FIG. 1B shows an antibody presentation phage.

As shown in FIG. 1B, each antibody-displayed phage contained in the antibody-displayed phage library aqueous solution has an antibody fragment on the surface thereof. It is desirable that each antibody-displayed phage has an scFv antibody fragment on the surface thereof. Each scFv antibody fragment consists of one heavy chain variable region 21 and one light chain variable region 31 which are randomly selected from plural types of heavy chain variable regions 21 and from plural types of light chain variable regions 31, respectively.

The plural kinds of antibody-displayed phages have different antibody fragments from each other.

Each antibody-displayed phage contains a phagemid vector. The phagemid vector has a gene sequence coding for the antibody fragment added on the surface thereof. Desirably, the phagemid vector has a VH gene coding for one heavy chain variable region 21 of the scFv antibody fragment and a VL gene coding for one light chain variable region 31 of the scFv antibody fragment.

Non Patent Literature 3, Non Patent Literature 4 and, Non Patent Literature 5 disclose a method for preparing such an antibody-displayed phage library aqueous solution. These skilled in the art who have read Non Patent Literature 3, Non Patent Literature 4, and Non Patent Literature 5 could prepare the antibody-displayed phage library aqueous solution easily.

[Non Patent Literature 3]

Greg Winter, Andrew D. Griffiths, Robert E. Hawkins, and Hennie R. Hoogenboom (1994) Making Antibodies by Phage Display Technology, Annual Review of Immunology, Vol. 12, 433-455

[Non Patent Literature 4]

Takayuki Okamoto, Yohei Mukai, Yasuo Yoshioka, Hiroko Shibata, Maki Kawamura, Yoko Yamamoto, Shinsaku Nakagawa, Haruhiko Kamada, Takao Hayakawa, Tadanori Mayumi, Yasuo Tsutsumi (2004) Optimal construction of non-immune scFv phage display libraries from mouse bone marrow and spleen established to select specific scFvs efficiently binding to antigen, Biochemical and Biophysical Research Communications, Vol. 323(2), 583-91

[Non Patent Literature 5]

Phage Display: A Practical Approach (The Practical Approach Series), Oxford University Press, USA (2004/5/6), ISBN 978-0199638734

As shown in FIG. 3, the antibody-displayed phage library aqueous solution is supplied to a support comprising polypeptide on the surface thereof. The polypeptide serves as an antigen. The antibody fragment added on the surface of the antibody-displayed phage is specifically bound to the polypeptide. In this way, at least a portion of the plural kinds of antibody-displayed phages are specifically bound to the polypeptide. It is desirable that the antibody-displayed phages which have not been bound to the polypeptide are removed by washing. It is desirable that a buffer solution is used for the washing. An example of the buffer solution is a PBS buffer solution containing Tween20 at a concentration of 0.1% by weight.

The polypeptide is immobilized on the support. It is desirable that the polypeptide is immobilized on the support through covalent bond. For example, a cysteine residue is introduced into the end of the polypeptide. Meanwhile, a gold film is formed on the support. A sulfur atom included in the cysteine residue reacts with the gold film to form a sulfide bond between the polypeptide and the gold film. In this way, the polypeptide can be immobilized on the support. Other immobilization methods can be used.

An example of the support is a substrate, a microbead, or a nonwoven fabric. An example of the materials of the substrate is plastic. Polypropylene is desirable. More particularly, an example of the support is an ELISA plate.

(Step (b))

Next, the support is heated to a temperature of not less than 37 degrees Celsius and not more than 70 degrees Celsius. When the heating temperature is high, the heating period is short. On the other hand, the heating period is long, when the heating temperature is low. More specifically, it is desirable that the support is heated to 60 degrees Celsius for approximately 30 minutes.

The present inventors discovered that the peptide consisting of the amino acid sequence represented by SEQ ID NO: 01 is heat-stable. The peptide consisting of the amino acid sequence represented by SEQ ID NO: 01 is not denatured, even when the peptide is heated to 70 degrees Celsius. See the example 2, which is described later.

Some of antibody-displayed phages are released from the support by the heating. The antibody-displayed phages which have been released from the support are not heat-stable antibody-displayed phages. It is desirable that the support is heated, while the support is in contact with a buffer solution. This is because the antibody-displayed phages which have been released from the support are dispersed or dissolved in the buffer solution easily.

On the other hand, the other antibody-displayed phages are not released from the support by the heating. In other words, the other antibody-displayed phages are left on the support, even when they are heated. The other antibody-displayed phages, which have been left on the support, are heat-stable antibody-displayed phages. In this way, the heat-stable antibody-displayed phages are left on the support selectively.

It is desirable that the support is washed at the end of the step (b). For the washing, it is desirable that a buffer solution is used. An example of the buffer solution is a PBS buffer solution containing Tween 20 at a concentration of 0.1% by weight.

(Step (c))

Finally, the heat-stable antibody-displayed phages left on the support selectively are collected. In order to collect the heat-stable antibody-displayed phages from the support, reagent which denatures proteins is used. An example of the reagent is an acid aqueous solution such as hydrochloric acid, or an urea aqueous solution. A suitable example of the reagent is a 0.1M glycine-hydrochloric acid buffer solution (pH: 2.2).

The support is immersed in the 0.1M glycine-hydrochloric acid buffer solution (pH: 2.2) for 10-30 minutes to release the heat-stable antibody-displayed phages from the support. In this way, the 0.1M glycine-hydrochloric acid buffer solution which contains the heat-stable antibody-displayed phages is obtained.

Subsequently, the pH of the glycine-hydrochloric acid buffer solution is adjusted with an alkaline aqueous solution. It is desirable that the pH is adjusted to 7. An example of the alkaline aqueous solution is 1M Tris hydrochloric acid buffer solution (pH: 9.1).

Figure 2:
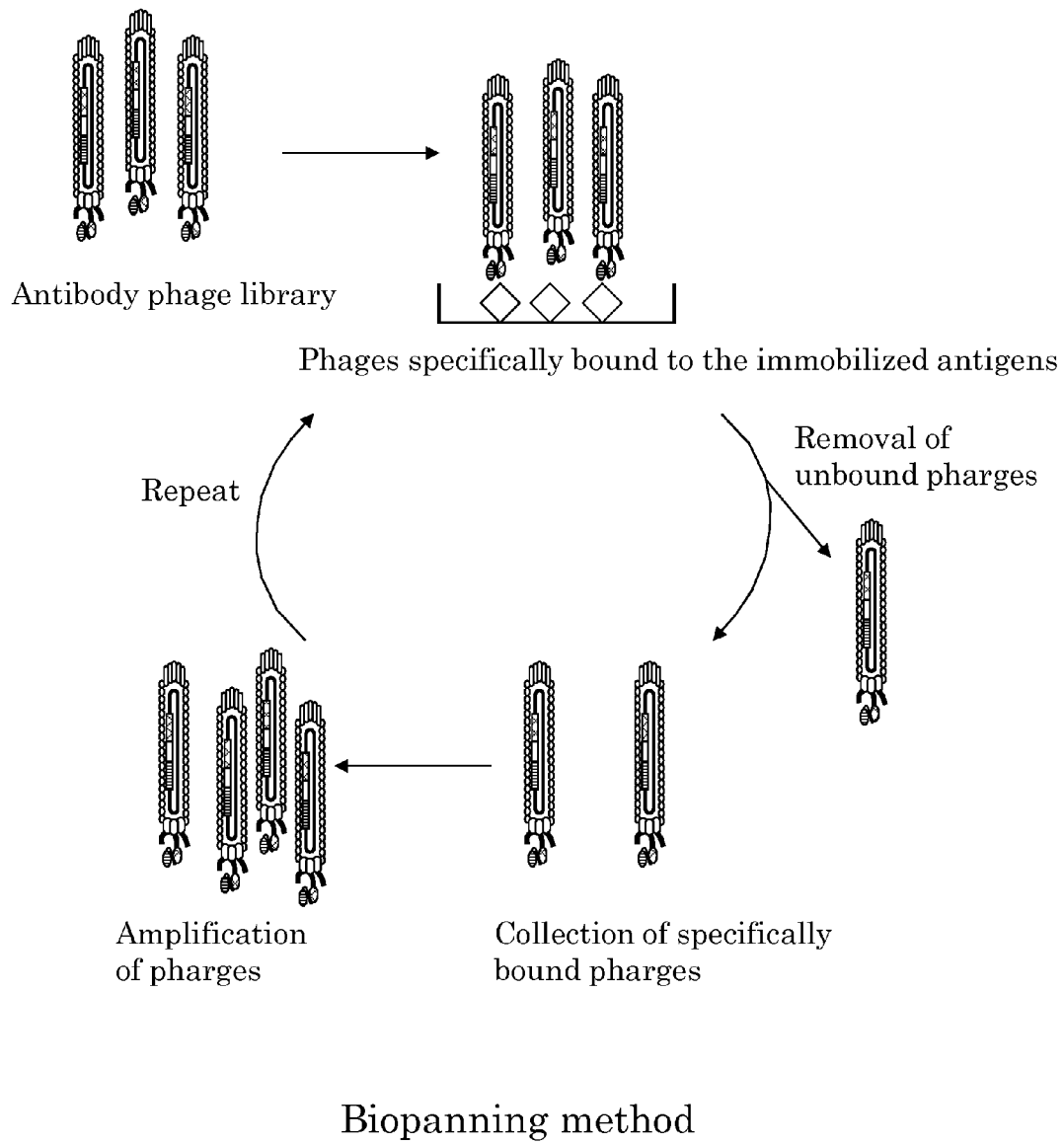
FIG. 2 shows a biopanning method.

As shown in FIG. 2, it is desirable that the collected heat-stable antibody-displayed phages are amplified.

Finally, using the collected heat-stable antibody-displayed phages, a heat-stable antibody fragment is obtained as below.

First, the collected heat-stable antibody-displayed phages are brought into contact with a cell (desirably, *E. coli*. TG-1) so as to produce an infected cell. By this infection, the *E. coli*. TG-1 acquires antibiotic-resistance.

Then, this infected cell is incubated to obtain a heat-stable antibody fragment.

Examples of the additional aspect of the present disclosure are as follows.

1st aspect: A method for acquiring a heat-stable antibody-displayed phage, the method comprising steps of:

(a) supplying an antibody-displayed phage library aqueous solution containing plural types of antibody-displayed phages to a support comprising a polypeptide on the surface thereof, so as to bind the plural types of the antibody-displayed phages to the polypeptide specifically; wherein each antibody-displayed phage comprises proteins containing a phagemid vector in the inside thereof;

each antibody-displayed phage comprises an antibody fragment on the external surface thereof; and the phagemid vector has a gene sequence coding for the antibody fragment;

(b) heating the support to the temperature of not less than 37 degrees Celsius and not more than 70 degrees Celsius, so as to release a portion of the antibody-displayed phages from the support and so as to leave the other antibody-displayed phages on the support selectively; and (c) collecting the other antibody-displayed phages which has been left on the support selectively in the step (b) so as to obtain the heat-stable antibody-displayed phage.

2nd aspect: The method according to claim 1, wherein the polypeptide consists of an amino acid sequence represented by SEQ ID NO: 01.

3rd aspect: The method according to claim 1, further comprising the following step between the step (a) and the step (b), a step of removing an antibody-displayed phages which have not been bound to the polypeptide specifically in the step (a).

4th aspect: The method according to claim 1, further comprising the following step between the step (b) and the step (c), a step of washing the support.

5th aspect: The method according to claim 1, further comprising the following step after the step (c), a step of amplifying the heat-stable antibody-displayed phages collected in the step (c).

6th aspect: A method for acquiring a heat-stable antibody fragment, the method comprising steps of:

(a) supplying an antibody-displayed phage library aqueous solution containing plural types of antibody-displayed phages to a support comprising a polypeptide on the surface thereof, so as to bind the plural types of the antibody-displayed phages to the polypeptide specifically; wherein each antibody-displayed phage comprises proteins containing a phagemid vector in the inside thereof;

each antibody-displayed phage comprises an antibody fragment on the external surface thereof; and the phagemid vector has a gene sequence coding for the antibody fragment;

(b) heating the support to the temperature of not less than 37 degrees Celsius and not more than 70 degrees Celsius, so as to release a portion of the antibody-displayed phages from the support and so as to leave the other antibody-displayed phages on the support selectively;

(c) collecting the other antibody-displayed phages which has been left on the support selectively in the step (b) so as to obtain the heat-stable antibody-displayed phage.

(d) bringing a cell into contact with the heat-stable antibody-displayed phages collected in the step (c) to produce an infected cell; and (e) incubating the infected cell produced in the step (d) to acquire the heat-stable antibody fragment.

7th aspect: A heat-stable peptide consisting of the amino acid sequence represented by SEQ ID NO: 01.

8th aspect: The heat-stable peptide according to claim 7, wherein the peptide is stable even when the peptide is heated to 70 degrees Celsius.

EXAMPLES

The following examples describe the present disclosure in more detail.

Example 1

Table 1, Table 2, Table 3, and Table 4 show the primers used in the example 1.

Table 1 shows the forward mixture primers A (primers 1-21, SEQ ID NOs: 02-22) for amplifying a light chain variable region.

Table 2 shows the forward mixture primers B (primers 22-44, SEQ ID NOs: 23-45) for amplifying a heavy chain variable region.

Table 3 shows the reverse mixture primers C (primers 45-49, SEQ ID NOs: 46-50) for amplifying a light chain variable region.

Table 4 shows the reverse mixture primers D (primers 50-55, SEQ ID NOs: 51-56) for amplifying a heavy chain variable region.

TABLE 1

```
Primer 1   SEQ ID  CCTTTCTATGCGGCCCAGCCGGCCATGGCCGAYA
           NO: 02  TTGTWCTCWCCCARTC Primer 2   SEQ ID  CCTTTCTATGCGGCCCAGCCGGCCATGGCCGAYA
           NO: 03  TTSTGMTSACYCAGTC Primer 3   SEQ ID  CCTTTCTATGCGGCCCAGCCGGCCATGGCCGAYA
           NO: 04  TTGTGMTMACTCAGTC Primer 4   SEQ ID  CCTTTCTATGCGGCCCAGCCGGCCATGGCCGAYA
           NO: 05  TTGTGHTRWCACAGTC Primer 5   SEQ ID  CCTTTCTATGCGGCCCAGCCGGCCATGGCCGAYA
           NO: 06  TTGTRATGACMCAGTC Primer 6   SEQ ID  CCTTTCTATGCGGCCCAGCCGGCCATGGCCGAYA
           NO: 07  TTMAGATRAMCCAGTC Primer 7   SEQ ID  CCTTTCTATGCGGCCCAGCCGGCCATGGCCGAYA
           NO: 08  TTCAGATGAYDCAGTC Primer 8   SEQ ID  CCTTTCTATGCGGCCCAGCCGGCCATGGCCGAYA
           NO: 09  TTTTGCTGACTCAGTC Primer 9   SEQ ID  CCTTTCTATGCGGCCCAGCCGGCCATGGCCGAYA
           NO: 10  TTGTTCTCAWCCAGTC Primer 10  SEQ ID  CCTTTCTATGCGGCCCAGCCGGCCATGGCCGAYA
           NO: 11  TTGWGCTSACCCAATC Primer 11  SEQ ID  CCTTTCTATGCGGCCCAGCCGGCCATGGCCGAYA
           NO: 12  TTSTRATGACCCARTC Primer 12  SEQ ID  CCTTTCTATGCGGCCCAGCCGGCCATGGCCGAY
           NO: 13  RTTKTGATGACCCAVAC Primer 13  SEQ ID  CCTTTCTATGCGGCCCAGCCGGCCATGGCCGAYA
           NO: 14  TYCAGATGACACAGAC Primer 14  SEQ ID  CCTTTCTATGCGGCCCAGCCGGCCATGGCCGAYA
           NO: 15  TTGTGATGACACAACC Primer 15  SEQ ID  CCTTTCTATGCGGCCCAGCCGGCCATGGCCGAYA
           NO: 16  TCCAGCTGACTCAGCC
```

TABLE 1-continued

```
Primer 16  SEQ ID  CCTTTCTATGCGGCCCAGCCGGCCATGGCCGAYA
           NO: 17  TTGTGATGACBCAGKC Primer 17  SEQ ID  CCTTTCTATGCGGCCCAGCCGGCCATGGCCGAYA
           NO: 18  TTGTGATAACYCAGGA Primer 18  SEQ ID  CCTTTCTATGCGGCCCAGCCGGCCATGGCCGAYA
           NO: 19  TTGTGATGACCCAGWT Primer 19  SEQ ID  CCTTTCTATGCGGCCCAGCCGGCCATGGCCGAY
           NO: 20  GTGSTGMTSACYCAGTC Primer 20  SEQ ID  CCTTTCTATGCGGCCCAGCCGGCCATGGCCGAY
           NO: 21  GCTGTTGTACTCAGGAATC Primer 21  SEQ ID  CCTTTCTATGCGGCCCAGCCGGCCATGGCCGAYA
           NO: 22  TTGTDHTVWCHCAGTC
```

TABLE 2

```
Primer 22  SEQ ID  AGCGGCGGCGGCGGCTCTGGTGGTGGTGGATCC
           NO: 23  GAKGTRMAGCTTCAGGAGYC Primer 23  SEQ ID  AGCGGCGGCGGCGGCTCTGGTGGTGGTGGATCC
           NO: 24  GAGGTNCAGCTBCAGCAGTC Primer 24  SEQ ID  AGCGGCGGCGGCGGCTCTGGTGGTGGTGGATCC
           NO: 25  CAGGTGCAGCTGAAGSASTC Primer 25  SEQ ID  AGCGGCGGCGGCGGCTCTGGTGGTGGTGGATCC
           NO: 26  CAGSTBCAGCTGCAGCAGTC Primer 26  SEQ ID  AGCGGCGGCGGCGGCTCTGGTGGTGGTGGATCC
           NO: 27  GAGGTYCAGCTYCAGCAGTC Primer 27  SEQ ID  AGCGGCGGCGGCGGCTCTGGTGGTGGTGGATCC
           NO: 28  GARGTCCARCTGCAACARTC Primer 28  SEQ ID  AGCGGCGGCGGCGGCTCTGGTGGTGGTGGATCC
           NO: 29  CAGGTYCAGCTBCAGCARTC Primer 29  SEQ ID  AGCGGCGGCGGCGGCTCTGGTGGTGGTGGATCC
           NO: 30  CAGGTYCARCTKCAGCAGTC Primer 30  SEQ ID  AGCGGCGGCGGCGGCTCTGGTGGTGGTGGATCC
           NO: 31  CAGGTCCACGTGAAGCAGTC Primer 31  SEQ ID  AGCGGCGGCGGCGGCTCTGGTGGTGGTGGATCC
           NO: 32  GAGGTGAASSTGGTGGARTC Primer 32  SEQ ID  AGCGGCGGCGGCGGCTCTGGTGGTGGTGGATCC
           NO: 33  GAVGTGAWGYTGGTGGAGTC Primer 33  SEQ ID  AGCGGCGGCGGCGGCTCTGGTGGTGGTGGATCC
           NO: 34  GAGGTGAAGGTCATCGAGTC Primer 34  SEQ ID  AGCGGCGGCGGCGGCTCTGGTGGTGGTGGATCC
           NO: 35  SAGGTGCAGSKGGTGGAGTC Primer 35  SEQ ID  AGCGGCGGCGGCGGCTCTGGTGGTGGTGGATCC
           NO: 36  GAKGTGCAMCTGGTGGAGTC Primer 36  SEQ ID  AGCGGCGGCGGCGGCTCTGGTGGTGGTGGATCC
           NO: 37  GAAGTGCAVCTGGTGGAGTC Primer 37  SEQ ID  AGCGGCGGCGGCGGCTCTGGTGGTGGTGGATCC
           NO: 38  GAGGTGAAGCTGATGGARTC Primer 38  SEQ ID  AGCGGCGGCGGCGGCTCTGGTGGTGGTGGATCC
           NO: 39  GAGGTGCARCTTGTTGAGTC Primer 39  SEQ ID  AGCGGCGGCGGCGGCTCTGGTGGTGGTGGATCC
           NO: 40  GARGTRAAGCTTCTCGAGTC Primer 40  SEQ ID  AGCGGCGGCGGCGGCTCTGGTGGTGGTGGATCC
           NO: 41  GAAGTGAARSTTGAGGAGTC
```

TABLE 2-continued

| | | |
|---|---|---|
| Primer 41 | SEQ ID NO: 42 | AGCGGCGGCGGCGGCTCTGGTGGTGGTGGATCC GAAGTGATGCTGGTGGAGTC |
| Primer 42 | SEQ ID NO: 43 | AGCGGCGGCGGCGGCTCTGGTGGTGGTGGATCC CAGGTTACTCTRAAAGWGTSTG |
| Primer 43 | SEQ ID NO: 44 | AGCGGCGGCGGCGGCTCTGGTGGTGGTGGATCC CAGGTCCAAYTVCAGCARCC |
| Primer 44 | SEQ ID NO: 45 | AGCGGCGGCGGCGGCTCTGGTGGTGGTGGATCC GATGTGAACTTGGAAGTGTC |

TABLE 3

| | | |
|---|---|---|
| Primer 45 | SEQ ID NO: 46 | ACCAGAGCCGCCGCCGCCGCTACCACCACCACCC CGTTTGATTTCCARCTTKG |
| Primer 46 | SEQ ID NO: 47 | ACCAGAGCCGCCGCCGCCGCTACCACCACCACCC CGTTTTATTTCCAGCTTGG |
| Primer 47 | SEQ ID NO: 48 | ACCAGAGCCGCCGCCGCCGCTACCACCACCACCC CGTTTSAGCTCCAGCTTGG |
| Primer 48 | SEQ ID NO: 49 | ACCAGAGCCGCCGCCGCCGCTACCACCACCACCC CGTTYWATTTCCAACTTWG |
| Primer 49 | SEQ ID NO: 50 | ACCAGAGCCGCCGCCGCCGCTACCACCACCACCC CCTAGGACAGTCAGTTTGG |

TABLE 4

| | | |
|---|---|---|
| Primer 50 | SEQ ID NO: 51 | CGGCACCGGCGCACCTGCGGCCGCYGAGGAAACG GTGACCGTGGT |
| Primer 51 | SEQ ID NO: 52 | CGGCACCGGCGCACCTGCGGCCGCYGAGGAGACT GTGAGAGTGGT |
| Primer 52 | SEQ ID NO: 53 | CGGCACCGGCGCACCTGCGGCCGCYGAGGAGACG GTGACTGAGRT |
| Primer 53 | SEQ ID NO: 54 | CGGCACCGGCGCACCTGCGGCCGCYGAGGAAGAC TGTAGAGTGGT |
| Primer 54 | SEQ ID NO: 55 | CGGCACCGGCGCACCTGCGGCCGCYGCGGAGACA STGACCAGAGT |
| Primer 55 | SEQ ID NO: 56 | CGGCACCGGCGCACCTGCGGCCGCYGCAGAGACA STGACCAGAGT |

Step (a-1) Preparation of Total RNA from Mouse Spleen Immunized at Troponin I Derived from Human Myocardium The polypeptide (SEQ ID NO: 01, available from Sigma Aldrich Japan Co., Ltd., CAPAPIRRRSSNYRAYATEPHA-KKKSKISASRKLQLKTLLLQIAK) contained in troponin I derived from human myocardium was connected to human serum albumin (purchased from Sigma Aldrich Japan Co. Ltd.) using a sulfo-SMCC cross linker (purchased from Servo Fischer Scientific Co., Ltd.).

More particularly, the sulfo-SMCC cross linker (0.5 mg) was dissolved in a phosphate buffered saline of 100 microliter so as to obtain a first aqueous solution. This first aqueous solution was left under a temperature of 50 degrees Celsius for ten minutes.

The human serum albumin (10 mg) was dissolved in one milliliter of a phosphate buffered saline to obtain a second aqueous solution.

The first aqueous solution was mixed with the second aqueous solution to obtain the mixture. The mixture was left at rest for 30 minutes. In this way, the sulfo-SMCC cross linker was connected to the human serum albumin.

The mixture was passed through a column (purchased from GE health care, trade name: PD10) to remove the unreacted sulfo-SMCC cross linker.

The above-mentioned polypeptide (SEQ ID NO: 01, 1.5 mg) was dissolved in dimethylsulfoxide (hereinafter, referred to as "DMSO") to obtain a DMSO solution. The DMSO solution (100 microliters) was added to the mixture (1 mL) having a concentration of 2 mg/ml. Afterwards, the mixture is left overnight to connect the sulfo-SMCC cross linker to the amino acid (SEQ ID NO: 01).

In this way, human serum albumin modified with the polypeptide sequence (SEQ ID NO: 01) contained in the troponin I was obtained. Hereinafter, this human serum albumin is referred to as "troponin-modified HSA".

A complete Freud adjuvant (purchased from Wako Pure Chemical Industries Co., Ltd.) and troponin-modified HSA were mixed to obtain a mixture. This mixture was injected to a BALB/c mouse. The BALB/c mouse is a kind of the albino mouse.

Two weeks later, a mixture of phosphate buffered saline (hereinafter, referred to as "PBS") and troponin-modified HSA was injected to the BALB/c mouse. This was repeated once again. In this way, the BALB/c mouse was immunized by troponin-modified HSA for one month. In other words, by injecting the mixture to the BALB/c mouse, antibodies for troponin-modified HSA were produced in the body of the BALB/c mouse.

The spleen of the immunized BALB/c mouse was taken out. One milliliter of TRIzol (Purchased from Invitrogen Co., Ltd.) was added to the spleen and stirred well.

Then, a chloroform liquid having a volume of 0.2 mL (degree of purity: 99.9%) was added to this mixture containing the spleen, and the mixture was stirred well again.

The mixture was subjected to a centrifugal separation at an acceleration of gravity of 117,600 m/s$^2$ under a temperature of 4 degrees Celsius for 15 minutes. The supernatant (500 μL) was acquired. Isopropanol (500 μL) was added to the obtained supernatant and left at rest under a room temperature for ten minutes.

The supernatant was subject to a centrifugal separation having a condition identical to the above-mentioned condition to obtain a precipitate. A seventy-five percent ethanol aqueous solution (1 mL) was added to the obtained precipitate so as to obtain an ethanol solution.

The ethanol solution was subjected to a centrifugal separation at an acceleration of gravity of 73,500 m/s$^2$ for five minutes. The precipitate was dried. In this way, total mouse RNAs were obtained.

Step (a-2) Extract of mRNA from the Total Mouse Spleen mRNAs

Using an Oligotex™-dT30 <Super> mRNA Purification kit (purchased from Takara bio Co., Ltd.), an mRNA was extracted from the total mouse RNAs obtained in the step (a-1).

RNase-free water (100 μL) was injected into a microtube. This microtube was set at a block incubater (purchased from ASTEC CO. LTD.) and heated under a temperature of 70 degrees Celsius for one hour.

The total mouse RNAs were dissolved in the RNase-free water (100 μL).

A 2× binding buffered solution (100 μL) included in the kit and an oligotex (10 μL) included in the kit were mixed with the RNase-free water (100 μL). Subsequently, the mixture was left at rest under a temperature of 70 degrees Celsius for three minutes. Furthermore, the mixture was left at rest under a room temperature for ten minutes.

The mixture was subjected to a centrifugal separation at an acceleration of gravity of 147,000 m/s² for five minutes. The supernatant was removed, and the precipitate was suspended in Wash buffer (350 μL) included in the kit. The suspension liquid was supplied to a column included in the kit. The column was subjected to a centrifugal separation at an acceleration of gravity of 147,000 m/s² for 30 seconds.

The Wash buffer (350 μL) was supplied to the column to wash the column. The column was subjected to a centrifugal separation at an acceleration of gravity of 147,000 m/s² again for 30 seconds.

A microtube for sample collection was attached to the bottom of the column.

In order to extract mRNA contained in the column, RNase-free water (20 μL) contained in the microtube was supplied to the column. Subsequently, the column was subjected to a centrifugal separation at an acceleration of gravity of 147,000 m/s² for three minutes. Again, RNase-free water (20 μL) was supplied to the column, and the column was subjected to a centrifugal separation at an acceleration of gravity of 147,000 m/s² for three minutes.

Thus, the extract liquid containing the mRNA was obtained in the microtube.

(Step (a-3) Reverse-Transcription from mRNA to cDNA)

The mRNA contained in the obtained extract liquid was reverse-transcripted with reverse-transcriptase (purchased from Takara bio Co., Ltd, trade name: Prime Script) to obtain a solution containing cDNA.

Step (a-4-1) Amplification of the Gene Coding for the Light Chain Variable Region Using the cDNA The gene fragment (hereinafter, referred to as "VL gene fragment") coding for the light chain variable region was amplified by a PCR method using the cDNA contained in the solution, the forward mixture primers A (SEQ ID NOs: 02-22), and the reverse mixture primers C (SEQ ID NOs: 46-50). The polymerase used in this PCR method was purchased from Takara bio Co., Ltd as a trade name of TaKaRa Ex Taq Hot start Version.

The protocol of this PCR method is shown in Table 5.

TABLE 5

| One cycle | ninety six degrees Celsius for thirty seconds |
| | fifty two degrees Celsius for one minute |
| | sixty eight degrees Celsius for one minute |

The number of the cycle: 35 times.

Finally, the solution was left at 68 degrees Celsius for four minutes. In this way, a PCR solution was obtained. This PCR solution contained the amplified VL gene fragment.

For the confirmation and purification of the amplified VL gene fragment, the obtained PCR solution was subjected to an electrophoresis using a gel containing agarose having a concentration of 2% by weight.

Step (a-4-2) Amplification of the Gene Coding for the Heavy Chain Variable Region Using the cDNA The gene fragment (hereinafter, referred to as "VH gene fragment") coding for the heavy chain variable region was amplified by a PCR method using the cDNA contained in the solution, the forward mixture primers B (SEQ ID NOs: 23-45), and the reverse mixture primers C(SEQ ID NOs: 51-56). The polymerase used in this PCR method was purchased from Takara bio Co., Ltd as a trade name of TaKaRa Ex Taq Hot start Version.

The protocol of this PCR method was identical to that of the VL gene fragment.

Finally, the solution was left at 68 degrees Celsius for four minutes. In this way, a PCR solution was obtained. This PCR solution contained the amplified VH gene fragments.

For the confirmation of the generation of the VH gene fragments and for the purification of the VH gene fragments, the obtained PCR solution was subjected to an electrophoresis using a gel containing agarose having a concentration of 2% by weight.

Step (a-5) Connection of the VL Gene Fragment and the VH Gene Fragment

The purified VH gene fragment was connected to the purified VL gene fragment using an overlap extension PCR method. In this way, the gene fragment (hereinafter, referred to as "scFv gene fragment") coding for the scFv antibody fragment was obtained. The 5'-end and 3'-end of the obtained gene fragment was modified with restriction enzyme sites SfiI and NotI, respectively.

Step (a-6) Introduction of scfv gene to a vector

The scFv gene fragment was ligated into a phagemid vector having an ampicilin resistance gene.

More particularly, used was a vector equivalent to the phagemid vector disclosed in Non Patent Literature 6. The scFv antibody fragment was expressed as a fusion protein of phage coat protein g3p.

[Non Patent Literature 6]

Huan Qi, Haiqin Lu, Hua-Ji Qiu, Valery Petrenko, Aihua Liu (2012) Phagemid Vectors for Phage Display: Properties, Characteristics and Construction, Journal of Molecular Biology, Vol. 417(3), 129-143

First, the scFv gene fragment was treated with restriction enzymes SfiI and NotI (both of which were purchased from Takara bio Co., Ltd.). The scFv gene fragment was purified by an electrophoresis method to obtain an aqueous solution containing the scFv gene fragment.

The phagemid vector was also treated with restriction enzymes SfiI and NotI (both of which were purchased from Takara bio Co., Ltd.). The phagemid vector was also purified by an electrophoresis method to obtain an aqueous solution containing the phagemid vector.

These two aqueous solutions were mixed to obtain a mixture.

An enzyme (purchased from Toyobo Co., Ltd., trade name: Ligation High ver. 2) was added to the mixture, and the mixture was left under a temperature of 16 degrees Celsius for two hours. In this way, the scFv gene fragment was ligated into the phagemid vector.

*Escherichia coli* TG-1 cells were transformed with the ligated products by an electroporation method. Subsequently, the *Escherichia coli* was incubated overnight on a 2TYAG plate culture medium.

The 2TYAG plate culture medium was an agar medium containing the reagents shown in Table 6.

TABLE 6

| Reagent 2TY culture medium | Concentration |
|---|---|
| Ampicillin | 100 μg/ml |
| Glucose | 2% |

(Step (a-7) Preparation of Antibody-Displayed Phage Library Aqueous Solution)

All the colonies formed on the 2TYAG plate culture medium were collected. The collected colonies were suspended in a PBS solution containing glycerol at a concentration of 15% by weight.

A portion of the collected *Escherichia coli* solution was added to a 2TYAG liquid medium having a volume of 30 milliliters. Subsequently, the *Escherichia coli* was incubated until it reached log-phase. M13K07 helper phase (available from Invitrogen) was added to the *Escherichia coli* solution in such a manner that the multiplicity of infection (MOI) was 10. The *Escherichia coli* solution was left at rest under a temperature of 37 degrees Celsius for thirty minutes. Furthermore, the *Escherichia coli* solution was incubated with shaking under a temperature of 37 degrees Celsius for thirty minutes. The supernatant was left by centrifugation. The precipitate containing the *Escherichia coli* was suspended again in the 2TYAK liquid medium. The *Escherichia coli* was incubated for over night under a temperature of 30 degrees Celsius.

The 2TYAK liquid culture medium contained the reagents shown in Table 7.

TABLE 7

| Reagent 2TY culture medium | Concentration |
| --- | --- |
| Ampicillin | 100 µg/ml |
| Kanamycin | 50 µg/ml |

Next, the liquid culture was centrifuged to collect the supernatant. A NaCl aqueous solution having a concentration of 2.5 M and a polyethylene glycol 6000 aqueous solution having a concentration of 20% (weight/volume) were added to this supernatant. After the mixture was stirred well, the mixture was left at rest under a temperature of 4 degrees Celsius for six hours.

Subsequently, the mixture is centrifuged to collect the precipitate. This precipitate was dissolved in a PBS aqueous solution having a volume of approximately 1 milliliter. Furthermore, the PBS aqueous solution is centrifuged to remove the precipitate of the *Escherichia coli*. In this way, the supernatant was obtained as the antibody-displayed phage library aqueous solution.

(Step (a-8): Binding of the Antibody-Displayed Phage Library to the Support)

A support where a polypeptide was immobilized was prepared as below, using an ELISA plate (trade name: Maleimide Activated 96-well plates, available from Termoscoenmtific company).

The polypeptide consisting of the amino acid sequences represented by SEQ ID NO: 01 was immobilized on the ELISA plate with accordance with the protocol of the ELISA plate as below.

First, the ELISA plate was washed three times with a 0.1M sodium phosphate buffer solution (pH: 7.2) containing Tween20 (0.05%) and NaCl (150 mM).

Polypeptide (SEQ ID NO: 01, powder, 1 milligram) was dissolved in DMSO (100 microliters) to obtain a polypeptide solution.

Then, the polypeptide aqueous solution containing reagents shown in following Table 8 was prepared.

TABLE 8

| Reagent | Concentration |
| --- | --- |
| Polypeptide solution | 2 µg/ml |
| Sodium chloride | 150 mM |
| EDTA | 15 mM |
| Sodium phosphate buffer solution (pH: 7.2) | 0.1M |
| Total volume | 150 microliters |

The polypeptide aqueous solution was supplied to the ELISA plate, and the polypeptide aqueous solution was left at rest under temperature of 4 degrees Celsius overnight. In this way, a polypeptide-immobilized support was prepared.

The ELISA plate was washed three times with a 0.1M sodium phosphate buffer solution (pH: 7.2) containing Tween20 (0.05%) and NaCl (150 mM).

Then, a cysteine aqueous solution containing reagents shown in the following Table 9 was prepared.

TABLE 9

| Reagent | Concentration |
| --- | --- |
| Cysteine | 10 µg/ml |
| Sodium chloride | 150 mM |
| EDTA | 15 mM |
| Sodium phosphate buffer solution (pH: 7.2) | 0.1M |
| Total volume | 200 microliters |

The cysteine aqueous solution was supplied to the ELISA plate. Subsequently, the cysteine aqueous solution was left under a room temperature for one hour.

The ELISA plate was washed three times with a 0.1M sodium phosphate buffer solution (pH: 7.2) containing Tween20 (0.05%) and NaCl (150 mM).

Then, bovine serum albumin (hereinafter, referred to as "BSA", 15 microliters) having a concentration of 5% (weight/volume) and the antibody-displayed phage library aqueous solution (75 microliter) prepared in the step (a-7) were mixed with a PBS aqueous solution. In the PBS solutions, the number of the antibody-displayed phages was $1 \times 10^{11}$ CFU. The mixed PBS aqueous solution (150 microliters) was added on the ELISA plate.

The ELISA plate was shook under a room temperature for one hour. Subsequently, the ELISA plate was washed ten times with a PBS aqueous solution containing Tween 20 at a concentration of 0.1% by weight (hereinafter, this PBS aqueous solution is referred is "PBST aqueous solution").

After the washing, a PBST aqueous solution (200 microliters) was added to the ELISA plate. Subsequently, the ELISA plate was sealed.

(Step (b): Heat Treatment)

The ELISA plate obtained in the step (a-8) was left under a temperature of 60 degrees Celsius for 30 minutes.

(Step (c): Collection of Heat-Stable Antibody-Displayed Phages)

After the step (b), a PBST aqueous solution was removed from the ELISA plate. The ELISA plate was washed five times with a PBST aqueous solution having a temperature of 60 degrees Celsius.

Then, a glycine-hydrochloric acid buffer solution (pH: 2.2, 200 microliters) having a concentration of 0.1M was added to the ELISA plate. Subsequently, the ELISA plate was left under a room temperature for ten minutes. This allowed the heat-stable antibody-displayed phages to be released from the ELISA plate. The glycine-hydrochloric acid buffer solution contained the heat-stable antibody-displayed phages.

Subsequently, the glycine-hydrochloric acid buffer solution was collected from the ELISA plate, and a Tris-HCl buffer solution (pH: 9.1) having a concentration of 1M was immediately added to the glycine-hydrochloric acid buffer solution so as to adjust the pH of the glycine-hydrochloric acid buffer solution to approximately 7.0. In this way, heat-stable antibody-displayed phages were provided.

In order to amplify the heat-stable antibody-displayed phages, the obtained heat-stable antibody-displayed phages were mixed well with an *Escherichia coli* TG-1 culture solution (30 mL). In this culture solution, the *Escherichia coli* TG-1 was incubated in advance so as to reach the log phase *Escherichia coli*.

After the mixing, this culture solution was left at rest under a temperature of 37 degrees Celsius for 30 minutes. Subsequently, the culture solution was centrifuged to remove the supernatant.

The precipitate containing the *Escherichia coli* TG-1 was suspended again with 2×TY liquid medium (1 mL). In this way, the *Escherichia coli* TG-1 infected with the heat-stable antibody-displayed phages were prepared.

This *Escherichia coli* TG-1 was incubated on the 2TYAG plate culture medium overnight.

Next, the step (a-7) was repeated next. More particularly, first, all the colonies formed on the 2TYAG plate culture medium were collected. Finally, the antibody-displayed phage library aqueous solution was obtained again.

A biopanning method was performed using the obtained antibody-displayed phage library aqueous solution. More particularly, prepared was an aqueous solution (150 microliters) of troponin I (purchased from Funakoshi) derived from human heart muscle. The concentration of this aqueous solution was adjusted in advance to 6.7 µg/ml with a 0.1M NaHCO$_3$ (pH: 8.3) aqueous solution.

The aqueous solution (150 microliters) of troponin I derived from human heart muscle was added to the ELISA plate (purchased from Costar). Subsequently, this ELISA plate was left under a temperature of 4 degrees Celsius overnight.

After the ELISA plate was washed with a PBS aqueous solution, a PBS aqueous solution (400 microliters) containing BSA at a concentration of 0.5% (weight/volume) was added to the ELISA plate. Subsequently, the ELISA plate was left under a room temperature for two hours. In this way, the ELISA plate where the troponin I was immobilized was prepared.

Then, BSA (30 microliter) having a concentration of 5% (weight/volume) was mixed with the antibody-displayed phage library aqueous solution (120 microliter). In the aqueous solution, the number of the antibody-displayed phages was 0.2×10^ 10 CFU. After the mixing, the aqueous solution (150 microliters) was added on the ELISA plate.

After the ELISA plate was shook under a room temperature for one hour, the ELISA plate was washed ten times with a PBST aqueous solution having a concentration of 0.1% by weight.

Subsequently, the PBST aqueous solution was collected from the ELISA plate, and a Tris-HCl buffer solution (pH: 9.1) having a concentration of 1M was immediately added to the PBST aqueous solution so as to adjust the pH of the PBST aqueous solution to approximately 7.0. In this way, heat-stable antibody-displayed phages were obtained.

In order to amplify the heat-stable antibody-displayed phages, the obtained heat-stable antibody-displayed phages were mixed with an *Escherichia coli* TG-1 culture solution (30 mL). In this culture solution, the *Escherichia coli* TG-1 was incubated in advance in such a manner that the *Escherichia coli* TG-1 reached log-phase.

After the mixing, this culture solution was left at rest under a temperature of 37 degrees Celsius for 30 minutes. The culture solution was centrifuged and the supernatant was removed.

The precipitate containing the *Escherichia coli* TG-1 was suspended again using 2×TY liquid medium (1 mL). In this way, the *Escherichia coli* TG-1 infected with the heat-stable antibody-displayed phage was prepared.

This *Escherichia coli* TG-1 was incubated on a 2TYAG plate medium overnight. In this way, a biopanning method was performed.

The colonies formed on the 2TYAG plate medium were collected. The sequence of the heat-stable antibody gene contained in the *Escherichia coli* TG-1 was analyzed. As a result, the light chain variable region sequence, the linker sequence, and the heavy chain variable region sequence of the collected heat-stable antibody gene were identified as SEQ ID NO: 60, SEQ ID NO: 61, and SEQ ID NO: 62, respectively.

```
Light chain variable region sequence
                                           (SEQ ID NO: 60)
GACGTGGTGATCACTCAGTCTCCACTCACTTTGTCGGTTACCATTGGACA

ACCAGCCTCCATCTCTTGCAAGTCAAGTCAGAGCCTCTTAGATAGTGATG

GAAAGACATATTTGAATTGGTTGTTACAGAGGCCAGGCCAGTCTCCAAAG

CGCCTAATCTATCTGGTGTCTAAACTGGACTCTGGAGTCCCTGACAGGTT

CACTGGCAGTGGATCAGGGACAGATTTCACACTGAAAATCAGCAGAGTGG

AGGCTGAGGATTTGGGAGTTTATTATTGCTGGCAAGGTACACATTTTCCT

CAGACGTTCGGTGGAGGCACCAAGCTGGAAATAAAACGG

Linker sequence
                                           (SEQ ID NO: 61)
GGTGGTGGTGGTAGCGGCGGCGGCGGCTCTGGTGGTGGTGGATCC Heavy chain variable region sequence
                                           (SEQ ID NO: 62)
GAGGTTCAGCTTCAGCAGTCTGGGGCGGAGCTTGCGAGGTCAGGGGCCTC

AGTCAAGTTGTCCTGCACAGCTTCTGGCTTCAACATTAAAGACTACTATA

TGAACTGGATGAGGCAGAGGCCTGAACAGGGCCTGGAGTGGATTGGATGG

ATTGATCCTGCGAATGGTGATACTGCATATGCCCCGAGGTTCCAGGTCAA

GGCCACTATGACTGCAGACAAATCCTCCAACACAGCCTACCTGCAGCTCA

GAAGCCTGACATCTGAGGACACTGCCGTCTATTACTGTAATGCTGATCTC

CCTATGGACCAGTGGGGTCAAGGAACCACGGTCACCGTTTCCTCG
```

A cell is transfected with the light chain variable region sequence '(SEQ ID NO: 60), the linker sequence (SEQ ID NO: 61), and the heavy chain variable region sequence (SEQ ID NO: 62) to obtain the scFv antibody fragment consisting of the light chain variable region amino acid sequence (SEQ ID NO: 63), the linker amino acid sequence (SEQ ID NO: 64) and the heavy chain variable region amino acid sequence (SEQ ID NO: 65).

Example 2-1

No Heat Treatment

Pursuant to the step (a-8), the ELISA plate was prepared. An aqueous solution containing an A2 antibody-displayed phage was supplied to the ELISA plate so that the A2 antibody-displayed phage was immobilized on the polypeptide (SEQ ID NO: 01) on the ELISA plate. The method for preparing the aqueous solution containing the A2 antibody-displayed phage is described later. As shown in FIG. 1B, the A2 antibody-displayed phage contains a plasmid vector having the A2 gene sequence. As shown in FIG. 1B, the A2 antibody-displayed phage comprises the A2 antibody fragment on the external surface thereof.

The ELISA plate was shook under a room temperature for one hour. Subsequently, the ELISA plate was washed ten times with a PBST aqueous solution having a concentration of 0.1% by weight.

BSA (500 microliters) having a concentration of 5% (weight/volume) and a HRP-modified anti-M13 antibody (available from GE health care company, 1 microliter) were mixed with a PBS aqueous solution. A part of the mixed PBS aqueous solution (150 microliters) was added on the ELISA plate.

The ELISA plate was shook under a room temperature for one hour. Subsequently, the ELISA plate was washed five times with a PBST aqueous solution having a concentration of 0.1% by weight.

3,3',5,5'-tetramethylbenzidine (hereinafter, referred to as "TMB", trade name: 1-Step Ultra TMB—ELISA Substrate, available from Thermo Scientific Co., Ltd) was added to the ELISA plate. Five minutes later, sulfuric acid was added. The absorbance of the ELISA plate at a wavelength of 450 nanometers was measured three times with a microplate reader (trade name: Infinite M200 PRO, available from Tecan Japan Co., Ltd.). The measured absorbance is shown in Table 10. In more detail, the absorbance measured in the first time, in the second time, and in the third time are shown in the columns of N=1, N=2, and N=3 of Table 10, respectively.

Example 2-2

25 Degrees Celsius and 5 Minutes

Pursuant to the step (a-8), the ELISA plate was prepared. An aqueous solution containing the A2 antibody-displayed phage was supplied to the ELISA plate so that the A2 antibody-displayed phage was immobilized on the polypeptide (SEQ ID NO: 01) on the ELISA plate.

The ELISA plate was shook under a room temperature for one hour. Subsequently, the ELISA plate was washed ten times with a PBST aqueous solution having a concentration of 0.1% by weight.

After the washing, an PBST aqueous solution (200 microliters) was added to the ELISA plate. Subsequently, the ELISA plate was sealed.

Subsequently, the ELISA plate was left under a temperature of 25 degrees Celsius for five minutes.

The PBST aqueous solution was removed from the ELISA plate. The ELISA plate was washed five times with a PBST aqueous solution having a temperature of 25 degrees Celsius.

Subsequently, BSA (500 microliters) having a concentration of 5% (weight/volume) and a HRP-modified anti-M13 antibody (available from GE health care company, 1 microliter) were mixed with a PBS aqueous solution. A part of the mixed PBS aqueous solution (150 microliters) was added on the ELISA plate.

The ELISA plate was shook under a room temperature for forty five minutes. Subsequently, the ELISA plate was washed five times with a PBST aqueous solution having a concentration of 0.1% by weight.

TMB was added to the ELISA plate. Five minutes later, sulfuric acid was added. Finally, similarly to that of the example 2-1, the absorbance of the ELISA plate was measured.

Example 2-3

25 Degrees Celsius and 10 Minutes

An experiment similar to the example 2-2 was performed, except that the ELISA plate was left under a temperature of 25 degrees Celsius for 10 minutes instead of leaving the ELISA plate under a temperature of 25 degrees Celsius for 5 minutes.

Example 2-4

25 Degrees Celsius and 15 Minutes

An experiment similar to the example 2-2 was performed, except that the ELISA plate was left under a temperature of 25 degrees Celsius for 15 minutes instead of leaving the ELISA plate under a temperature of 25 degrees Celsius for 5 minutes.

Example 2-5

25 Degrees Celsius and 20 Minutes

An experiment similar to the example 2-2 was performed, except that the ELISA plate was left under a temperature of 25 degrees Celsius for 20 minutes instead of leaving the ELISA plate under a temperature of 25 degrees Celsius for 5 minutes.

Example 2-6

25 Degrees Celsius and 30 Minutes

An experiment similar to the example 2-2 was performed, except that the ELISA plate was left under a temperature of 25 degrees Celsius for 30 minutes instead of leaving the ELISA plate under a temperature of 25 degrees Celsius for 5 minutes.

Example 2-7

25 Degrees Celsius and 60 Minutes

An experiment similar to the example 2-2 was performed, except that the ELISA plate was left under a temperature of 25 degrees Celsius for 60 minutes instead of leaving the ELISA plate under a temperature of 25 degrees Celsius for 5 minutes.

Example 2-8

37 Degrees Celsius and 5 Minutes

An experiment similar to the example 2-2 was performed, except that the following (a) and (b).

(a): the ELISA plate was left under a temperature of 37 degrees Celsius for 5 minutes, instead of leaving the ELISA plate under a temperature of 25 degrees Celsius for 5 minutes, and (b) the ELISA plate was washed with a PBST aqueous solution having a temperature of 37 degrees Celsius, instead of washing the ELISA plate with the PBST aqueous solution having a temperature of 25 degrees Celsius.

Example 2-9

37 Degrees Celsius and 10 Minutes

An experiment similar to the example 2-8 was performed, except that the ELISA plate was left under a temperature of 37 degrees Celsius for 10 minutes instead of leaving the ELISA plate under a temperature of 37 degrees Celsius for 5 minutes.

Example 2-10

37 Degrees Celsius and 15 Minutes

An experiment similar to the example 2-8 was performed, except that the ELISA plate was left under a temperature of 37 degrees Celsius for 15 minutes instead of leaving the ELISA plate under a temperature of 37 degrees Celsius for 5 minutes.

Example 2-11

37 Degrees Celsius and 20 Minutes

An experiment similar to the example 2-8 was performed, except that the ELISA plate was left under a temperature of 37 degrees Celsius for 20 minutes instead of leaving the ELISA plate under a temperature of 37 degrees Celsius for 5 minutes.

Example 2-12

37 Degrees Celsius and 30 Minutes

An experiment similar to the example 2-8 was performed, except that the ELISA plate was left under a temperature of 37 degrees Celsius for 30 minutes instead of leaving the ELISA plate under a temperature of 37 degrees Celsius for 5 minutes.

Example 2-13

37 Degrees Celsius and 60 Minutes

An experiment similar to the example 2-8 was performed, except that the ELISA plate was left under a temperature of 37 degrees Celsius for 60 minutes instead of leaving the ELISA plate under a temperature of 37 degrees Celsius for 5 minutes.

Example 2-14

50 Degrees Celsius and 5 Minutes

An experiment similar to the example 2-2 was performed, except that the following (a) and (b).

(a): the ELISA plate was left under a temperature of 50 degrees Celsius for 5 minutes, instead of leaving the ELISA plate under a temperature of 25 degrees Celsius for 5 minutes, and (b) the ELISA plate was washed with a PBST aqueous solution having a temperature of 50 degrees Celsius, instead of washing the ELISA plate with the PBST aqueous solution having a temperature of 25 degrees Celsius.

Example 2-15

50 Degrees Celsius and 10 Minutes

An experiment similar to the example 2-14 was performed, except that the ELISA plate was left under a temperature of 50 degrees Celsius for 10 minutes instead of leaving the ELISA plate under a temperature of 50 degrees Celsius for 5 minutes.

Example 2-16

50 Degrees Celsius and 15 Minutes

An experiment similar to the example 2-14 was performed, except that the ELISA plate was left under a temperature of 50 degrees Celsius for 15 minutes instead of leaving the ELISA plate under a temperature of 50 degrees Celsius for 5 minutes.

Example 2-17

50 Degrees Celsius and 20 Minutes

An experiment similar to the example 2-14 was performed, except that the ELISA plate was left under a temperature of 50 degrees Celsius for 20 minutes instead of leaving the ELISA plate under a temperature of 50 degrees Celsius for 5 minutes.

Example 2-18

50 Degrees Celsius and 30 Minutes

An experiment similar to the example 2-14 was performed, except that the ELISA plate was left under a temperature of 50 degrees Celsius for 30 minutes instead of leaving the ELISA plate under a temperature of 50 degrees Celsius for 5 minutes.

Example 2-19

50 Degrees Celsius and 60 Minutes

An experiment similar to the example 2-14 was performed, except that the ELISA plate was left under a temperature of 50 degrees Celsius for 60 minutes instead of leaving the ELISA plate under a temperature of 50 degrees Celsius for 5 minutes.

Example 2-20

60 Degrees Celsius and 5 Minutes

An experiment similar to the example 2-2 was performed, except that the following (a) and (b).

(a): the ELISA plate was left under a temperature of 60 degrees Celsius for 5 minutes, instead of leaving the ELISA plate under a temperature of 25 degrees Celsius for 5 minutes, and (b) the ELISA plate was washed with a PBST aqueous solution having a temperature of 60 degrees Celsius, instead of washing the ELISA plate with the PBST aqueous solution having a temperature of 25 degrees Celsius.

Example 2-21

60 Degrees Celsius and 10 Minutes

An experiment similar to the example 2-20 was performed, except that the ELISA plate was left under a temperature of 60 degrees Celsius for 10 minutes instead of leaving the ELISA plate under a temperature of 60 degrees Celsius for 5 minutes.

Example 2-22

60 Degrees Celsius and 15 Minutes

An experiment similar to the example 2-20 was performed, except that the ELISA plate was left under a temperature of 60 degrees Celsius for 15 minutes instead of leaving the ELISA plate under a temperature of 60 degrees Celsius for 5 minutes.

Example 2-23

60 Degrees Celsius and 20 Minutes

An experiment similar to the example 2-20 was performed, except that the ELISA plate was left under a temperature of 60 degrees Celsius for 20 minutes instead of leaving the ELISA plate under a temperature of 60 degrees Celsius for 5 minutes.

Example 2-24

60 Degrees Celsius and 30 Minutes

An experiment similar to the example 2-20 was performed, except that the ELISA plate was left under a temperature of 60 degrees Celsius for 30 minutes instead of leaving the ELISA plate under a temperature of 60 degrees Celsius for 5 minutes.

Example 2-25

60 Degrees Celsius and 60 Minutes

An experiment similar to the example 2-20 was performed, except that the ELISA plate was left under a temperature of 60 degrees Celsius for 60 minutes instead of leaving the ELISA plate under a temperature of 60 degrees Celsius for 5 minutes.

Example 2-26

70 Degrees Celsius and 5 Minutes

An experiment similar to the example 2-2 was performed, except that the following (a) and (b).

(a): the ELISA plate was left under a temperature of 70 degrees Celsius for 5 minutes, instead of leaving the ELISA plate under a temperature of 25 degrees Celsius for 5 minutes, and (b) the ELISA plate was washed with a PBST aqueous solution having a temperature of 70 degrees Celsius, instead of washing the ELISA plate with the PBST aqueous solution having a temperature of 25 degrees Celsius.

Example 2-27

70 Degrees Celsius and 10 Minutes

An experiment similar to the example 2-26 was performed, except that the ELISA plate was left under a temperature of 70 degrees Celsius for 10 minutes instead of leaving the ELISA plate under a temperature of 70 degrees Celsius for 5 minutes.

Example 2-28

70 Degrees Celsius and 15 Minutes

An experiment similar to the example 2-26 was performed, except that the ELISA plate was left under a temperature of 70 degrees Celsius for 15 minutes instead of leaving the ELISA plate under a temperature of 70 degrees Celsius for 5 minutes.

Example 2-29

70 Degrees Celsius and 20 Minutes

An experiment similar to the example 2-26 was performed, except that the ELISA plate was left under a temperature of 70 degrees Celsius for 20 minutes instead of leaving the ELISA plate under a temperature of 70 degrees Celsius for 5 minutes.

Example 2-30

70 Degrees Celsius and 30 Minutes

An experiment similar to the example 2-26 was performed, except that the ELISA plate was left under a temperature of 70 degrees Celsius for 30 minutes instead of leaving the ELISA plate under a temperature of 70 degrees Celsius for 5 minutes.

Example 2-31

70 Degrees Celsius and 60 Minutes

An experiment similar to the example 2-26 was performed, except that the ELISA plate was left under a temperature of 70 degrees Celsius for 60 minutes instead of leaving the ELISA plate under a temperature of 70 degrees Celsius for 5 minutes.

TABLE 10

| | Temperature (unit: Celsius degree) | Time (unit: minute) | Absorbance | | |
|---|---|---|---|---|---|
| | | | N = 1 | N = 2 | N = 3 |
| Example 2-1 | No heat treatment | — | 2.14 | 2.50 | 2.47 |
| Example 2-2 | 25 | 5 | 2.08 | 2.40 | 2.21 |
| Example 2-3 | 25 | 10 | 2.05 | 2.51 | 2.43 |
| Example 2-4 | 25 | 15 | 2.00 | 2.33 | 2.35 |
| Example 2-5 | 25 | 20 | 2.09 | 2.58 | 2.44 |
| Example 2-6 | 25 | 30 | 2.08 | 2.74 | 2.39 |
| Example 2-7 | 25 | 60 | 1.91 | 2.63 | 2.57 |
| Example 2-8 | 37 | 5 | 2.07 | 2.00 | 2.19 |
| Example 2-9 | 37 | 10 | 1.90 | 1.84 | 2.07 |
| Example 2-10 | 37 | 15 | 1.60 | 1.69 | 2.14 |
| Example 2-11 | 37 | 20 | 1.50 | 1.41 | 2.08 |
| Example 2-12 | 37 | 30 | 1.28 | 1.17 | 1.74 |
| Example 2-13 | 37 | 60 | 0.96 | 0.92 | 1.26 |
| Example 2-14 | 50 | 5 | 1.96 | 2.22 | 2.32 |
| Example 2-15 | 50 | 10 | 1.56 | 2.06 | 2.09 |
| Example 2-16 | 50 | 15 | 0.93 | 1.84 | 1.68 |
| Example 2-17 | 50 | 20 | 0.74 | 1.35 | 1.31 |
| Example 2-18 | 50 | 30 | 0.71 | 0.89 | 0.88 |
| Example 2-19 | 50 | 60 | 0.68 | 0.85 | 0.84 |

TABLE 10-continued

| | Temperature (unit: Celsius degree) | Time (unit: minute) | Absorbance N = 1 | N = 2 | N = 3 |
|---|---|---|---|---|---|
| Example 2-20 | 60 | 5 | 1.51 | 1.39 | 2.20 |
| Example 2-21 | 60 | 10 | 0.71 | 0.81 | 1.61 |
| Example 2-22 | 60 | 15 | 0.59 | 0.63 | 1.09 |
| Example 2-23 | 60 | 20 | 0.52 | 0.53 | 0.82 |
| Example 2-24 | 60 | 30 | 0.35 | 0.37 | 0.80 |
| Example 2-25 | 60 | 60 | 0.27 | 0.29 | 0.72 |
| Example 2-26 | 70 | 5 | 1.43 | 1.24 | 1.22 |
| Example 2-27 | 70 | 10 | 0.72 | 0.78 | 0.73 |
| Example 2-28 | 70 | 15 | 0.45 | 0.50 | 0.42 |
| Example 2-29 | 70 | 20 | 0.21 | 0.21 | 0.21 |
| Example 2-30 | 70 | 30 | 0.20 | 0.20 | 0.21 |
| Example 2-31 | 70 | 60 | 0.17 | 0.18 | 0.16 |

The absorbance corresponds to an amount of the A2 antibody-displayed phage left on the ELISA plate having the peptide consisting of the amino acid sequence represented by SEQ ID NO: 01 on the surface thereof. Higher absorbance means that more A2 antibody-displayed phages were left. On the contrary, lower absorbance means that less A2 antibody-displayed phages were left.

A phage binding ratio was calculated from Table 10 on the basis of the following formula (I):

Phage binding ratio (%)=Average absorbance of each example/Average absorbance of the example 2-1×100    (I)

Figure 5:
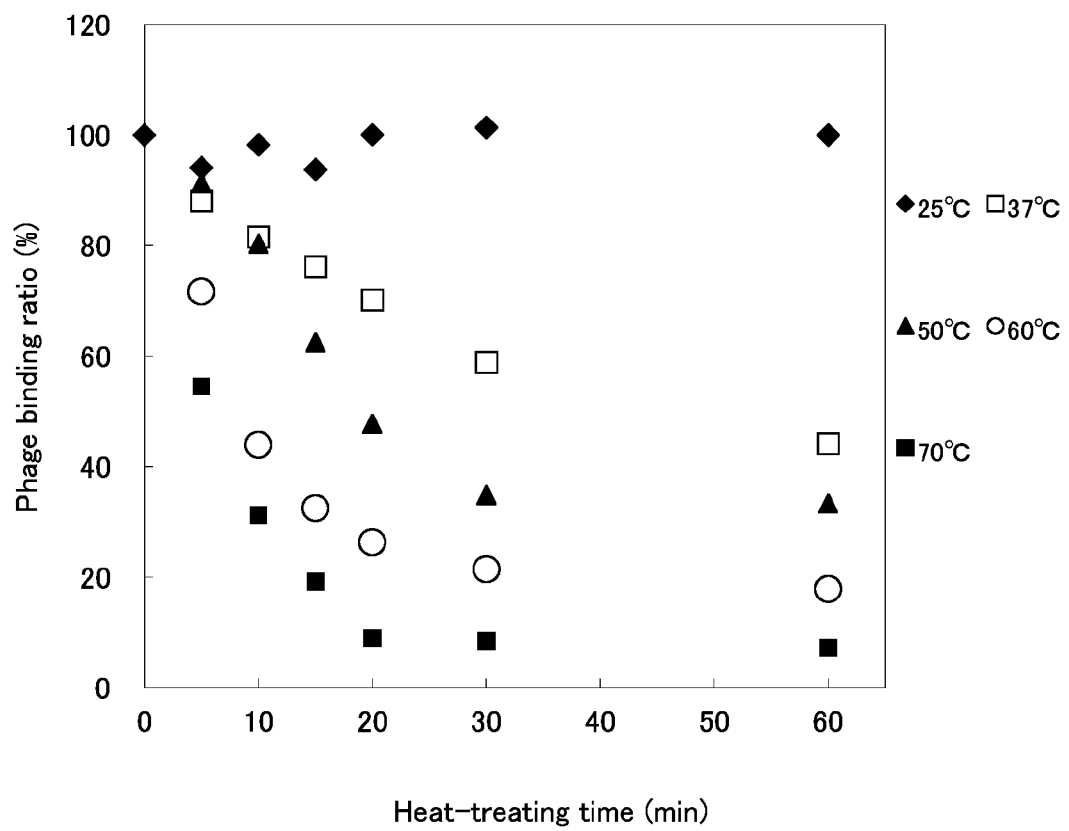
FIG. 5 shows a graph of the experimental result according to the example 2-2 to the example 2-30.

FIG. 5 shows a graph of the phage binding ratio calculated in the example 2-2 to the example 2-31.

As is clear from FIG. 5, a phage binding ratio of 40% or more is obtained in a condition of 70 degrees Celsius or less and 5 minutes or less, in a condition of 60 degrees Celsius or less and 10 minutes or less, in a condition of 50 degrees Celsius or less and 20 minutes or less, or in a condition of 37 degrees Celsius or less and 60 minutes or less. Accordingly, the peptide consisting of the amino acid sequence represented by SEQ ID NO: 01 can be used in a biopanning method conducted in the heat treatment condition of 70 degrees Celsius or less and 5 minutes or less, desirably in the heat treatment condition of 60 degrees Celsius or less and 10 minutes or less, more desirably in the heat treatment condition of 50 degrees Celsius or less and 20 minutes or less, most desirably in the heat treatment condition of 37 degrees Celsius or less and 60 minutes or less. It is desirable that the lower limit of the heating temperature is 25 degrees Celsius.

(Preparation of the Aqueous Solution Containing the A2 Antibody-Displayed Phage)

As above, the A2 antibody-displayed phage contains the plasmid vector having the A2 gene sequence. The A2 antibody-displayed phage comprises the A2 antibody fragment (one of scFv antibody fragment) on the external surface thereof.

The A2 gene sequence is described below.

(SEQ ID NO: 66)
GACGTGGTGCTCACTCAGTCTCCACTCACTTTGTCGGTTACCATTGGACA

ACCAGCCTCCATCTCTTGCAAGTCAAGTCAGAGCCTCTTAGATAGTGATG

GAAAGACATATTTGAATTGGTTGTTACAGAGGCCAGGCCAGTCTCCAAAG

CGCCTAATCTATCTGGTGTCTAAACTGGACTCTGGAGTCCCTGACAGGTT

CACTGGCAGTGGATCAGGGACAGATTTCACACTGAAAATCAGCAGAGTGG

AGGCTGAGGATTTGGGAGTTTATTATTGCTGGCAAGGTACACATTTTCCT

CTCACGTTCGGTGCTGGGACAAAGTTGGAAATTAAACGGGGTGGTGGTGG

TAGCGGCGGCGGCGGCTCTGGTGGTGGTGGATCCCAGCTGCAGCTGCAGC

AGTCTGGGGCAGAGCTTGTGAGGTCAGGGGCCTCAGTCAAGTTGTCCTGC

ACAGCTTCTGGCTTCAACATTAAAGACTACTATATGAACTGGGTGAAGCA

GAGGCCTGAACAGGGCCTGGAGTGGATTGGATGGATTGATCCTGCGAATG

GTGATACTGCATATGCCCCGAGGTTCCAGGTCAAGGCCACTATGACTGCA

GACAAATCCTCCAACACAGCCTACCTGCAGCTCAGCAGCCTGACATCTGA

GGACACTGCCGTCTATTACTGTAATGCTGATCTCCCTATGGACCAGTGGG

GTCAAGGAACCTCAGTCACCGTCTCCTCA

Pursuant to the step (a-1)-step (a-4) of the example 1, the purified VH gene fragment and the purified VL gene fragment were obtained.

The purified VH gene fragment was connected to the purified VL gene fragment using an overlap extension PCR method. In this way, the gene fragment (hereinafter, referred to as "scFv gene fragment") coding for the scFv antibody fragment of the above-mentioned monoclonal antibody was obtained. The obtained gene fragment were modified with restriction enzyme sites NcoI and NotI at the 5'-end and 3'-end thereof, respectively.

The scFv gene fragment was ligated into a protein expression vector (purchased from Takara bio Co., Ltd, trade name: pET22b(+)). The detail of the ligation is described below.

First, the scFv gene fragment was treated with restriction enzymes NcoI and NotI (both of which were purchased from Takara bio Co., Ltd.). The scFv gene fragment was purified by an electrophoresis method to obtain an aqueous solution containing the scFv gene fragment.

The protein expression vector was also treated with restriction enzymes NcoI and NotI (both of which were purchased from Takara bio Co., Ltd.). The protein expression vector was purified by an electrophoresis method to obtain an aqueous solution containing the protein expression vector.

These two aqueous solutions were mixed to obtain a mixture.

An enzyme (purchased from Toyobo Co., Ltd., trade name: Ligation High ver. 2) was added to the mixture, and the mixture was left under a temperature of 16 degrees Celsius for two hours. In this way, the scFv gene fragment was ligated into the protein expression vector.

*Escherichia coli* (purchased from Takara bio Co., Ltd., trade name; DH5a competent cell) was transformed with the protein expression vector in which the scFv gene fragment was thus ligated.

Subsequently, the *Escherichia coli* was incubated for sixteen hours on a LB plate culture medium containing ampicillin having a concentration of 100 μg/mL. After the incubation, single colony formed on the LB plate culture medium was picked up. The single colony was supplied to a LB liquid culture medium (5 mL) containing ampicillin having a concentration of 100 μg/mL, and the colony was incubated for 16 hours.

The protein expression vector pET22b(+) was extracted from this LB liquid culture medium using a kit (QIAGEN Co., Ltd. trade name: QIAprep spin miniprep kit).

The light chain variable region base sequence, the linker base sequence, and the heavy chain variable region base sequence of the A2 antibody gene contained in the extracted protein expression vector pET22b (+) were identified as SEQ ID NO: 67, SEQ ID NO: 68, and SEQ ID NO: 69, respectively.

```
Light chain variable region base sequence
                                         (SEQ ID NO: 67)
GACGTGGTGCTCACTCAGTCTCCACTCACTTTGTCGGTTACCATTGGACA

ACCAGCCTCCATCTCTTGCAAGTCAAGTCAGAGCCTCTTAGATAGTGATG

GAAAGACATATTTGAATTGGTTGTTACAGAGGCCAGGCCAGTCTCCAAAG

CGCCTAATCTATCTGGTGTCTAAACTGGACTCTGGAGTCCCTGACAGGTT

CACTGGCAGTGGATCAGGGACAGATTTCACACTGAAAATCAGCAGAGTGG

AGGCTGAGGATTTGGGAGTTTATTATTGCTGGCAAGGTACACATTTTCCT

CTCACGTTCGGTGCTGGGACAAAGTTGGAAATTAAACGG

Linker base sequence
                                         (SEQ ID NO: 68)
GGTGGTGGTGGTAGCGGCGGCGGCGGCTCTGGTGGTGGTGGATCC Heavy chain variable region sequence
                                         (SEQ ID NO: 69)
CAGCTGCAGCTGCAGCAGTCTGGGGCAGAGCTTGTGAGGTCAGGGGCCTC

AGTCAAGTTGTCCTGCACAGCTTCTGGCTTCAACATTAAAGACTACTATA

TGAACTGGGTGAAGCAGAGGCCTGAACAGGGCCTGGAGTGGATTGGATGG

ATTGATCCTGCGAATGGTGATACTGCATATGCCCCGAGGTTCCAGGTCAA

GGCCACTATGACTGCAGACAAATCCTCCAACACAGCCTACCTGCAGCTCA

GCAGCCTGACATCTGAGGACACTGCCGTCTATTACTGTAATGCTGATCTC

CCTATGGACCAGTGGGGTCAAGGAACCTCAGTCACCGTCTCCTCA
```

Next, the gene fragment coding for the scFv antibody fragment was amplified by a PCR method using the extracted protein expression vector pET22b(+), the forward primer 56 (SEQ ID NO: 57), and the reverse primer 57 (SEQ ID NO: 58). The polymerase used in this PCR method was purchased from Takara bio Co., Ltd as a trade name of TaKaRa Ex Taq Hot start Version.

TABLE 11

| Primer 56 | SEQ ID NO: 57 | TTAAAGGCCCAGCCGGCCATGGCTGACGTGGTG CTCACTCAGTCT |
|---|---|---|
| Primer 57 | SEQ ID NO: 58 | CTCGAGTGCGGCCGCTGA |

The protocol of this PCR method is described in Table 12.

TABLE 12

| 1 cycle | 96 degrees Celsius 30 seconds |
| | 52 degrees Celsius 1 minute |
| | 68 degrees Celsius 1 minute |

The number of the cycle: 30 times.

In this way, the gene fragment coding for the scFv antibody fragment was obtained. Hereinafter, this gene fragment is referred to as "scFv gene fragment". The 5'-end and 3'-end of the scfv gene fragment were modified with the restriction enzyme sites SfiI and NotI, respectively.

The scFv gene fragment was ligated into a phagemid vector having an ampicillin-resistance gene.

More particularly, a phagemid vector equivalent to the phagemid vector disclosed in Non Patent Literature 6 was used. The scFv antibody fragment was expressed as a fusion protein of the phage coat protein g3p.

First, the scFv gene fragment was treated with restriction enzymes SfiI and NotI (both of which were purchased from Takara bio Co., Ltd.). The scFv gene fragment was purified by electrophoresis to obtain an aqueous solution containing the scFv gene fragment.

The phagemid vector was also treated with restriction enzymes SfiI and NotI (both of which were purchased from Takara bio Co., Ltd.). The phagemid vector was also purified by electrophoresis to obtain an aqueous solution containing the phagemid vector.

These two aqueous solutions were mixed to obtain a mixture.

An enzyme (purchased from Toyobo Co., Ltd., trade name: Ligation High ver. 2) was added to the mixture, and the mixture was left under a temperature of 16 degrees Celsius for two hours. In this way, the scFv gene fragment was ligated into phagemid vector.

*Escherichia coli* TG-1 was transformed with the ligation products by an electroporation method. Subseqently, the *Escherichia coli* was incubated overnight on a 2TYAG plate medium (See Table 6).

A single colony formed on the 2TYAG platie medium was picked up.

The single colony was added to the 2TYAK liquid culture medium (See Table 7) having a volume of 30 milliliters. Subsequently, the *Escherichia coli* was incubated until the *Escherichia coli* reach log-phase. M13K07 helper phage (available from Invitrogen) was added to the *Escherichia coli* aqueous solution in such a manner that multiplicity of infection (MOI) was configured to be 10. The *Escherichia coli* aqueous solution was left at rest at 37 degrees Celsius for 30 minutes. Furthermore, the *Escherichia coli* aqueous solution was incubated with shaking at 37 degrees Celsius for 30 minutes. The supernatant was removed by centrifugal separation. Subsequently, the precipitate containing the *Escherichia coli* was suspended again to a 2TYAK liquid medium. The *Escherichia coli* was incubated under a temperature of 30 degrees Celsius overnight.

Then, the culture solution was centrifuged to collect the supernatant. An aqueous solution of NaCl having a concentration of 2.5M and an aqueous solution of polyethylene glycol 6000 having a concentration of 20% (weight/volume) were added to the supernatant. After the mixture was stirred well, the mixture was left at rest at 4 degrees Celsius for six hours.

Subsequently, the mixture was centrifuged to collect the precipitate. This precipitate was dissolved in a PBS aqueous solution having a volume of approximately 1 mL. Furthermore, the PBS aqueous solution was centrifuged to remove the precipitate of the *Escherichia coli*. In this way, the supernatant was obtained. This supernatant was the aqueous solution containing the antibody-displayed phage containing the A2 gene sequence.

INDUSTRIAL APPLICABILITY

The present method for acquiring a heat-stable antibody-displayed phage is useful for the antibody development in a pharmaceutical field and in a diagnostic reagent field.

What is claimed is:

1. A method for acquiring a heat-stable antibody-displayed phage, the method comprising steps of:
    (a) supplying an antibody-displayed phage library aqueous solution containing plural types of antibody-displayed phages to a support comprising a polypeptide on the surface thereof, so as to bind the plural types of the antibody-displayed phages to the polypeptide specifically; wherein
    the polypeptide consists of an amino acid sequence represented by SEQ ID NO: 01;
    each antibody-displayed phage comprises proteins containing a phagemid vector in the inside thereof;
    each antibody-displayed phage comprises an antibody fragment on the external surface thereof; and
    the phagemid vector has a gene sequence coding for the antibody fragment;
    (b) heating the support to the temperature of not less than 37 degrees Celsius and not more than 70 degrees Celsius, so as to release a portion of the antibody-displayed phages from the support and so as to leave the other antibody-displayed phages on the support selectively; and
    (c) collecting the other antibody-displayed phages which has been left on the support selectively in the step (b) so as to obtain the heat-stable antibody-displayed phage.

2. The method according to claim 1, further comprising the following step between the step (a) and the step (b),
    a step of removing an antibody-displayed phages which have not been bound to the polypeptide specifically in the step (a).

3. The method according to claim 1, further comprising the following step between the step (b) and the step (c), a step of washing the support.

4. The method according to claim 1, further comprising the following step after the step (c), a step of amplifying the heat-stable antibody-displayed phages collected in the step (c).

5. A method for acquiring a heat-stable antibody fragment, the method comprising steps of:
    (a) supplying an antibody-displayed phage library aqueous solution containing plural types of antibody-displayed phages to a support comprising a polypeptide on the surface thereof, so as to bind the plural types of the antibody-displayed phages to the polypeptide specifically; wherein
    the polypeptide consists of an amino acid sequence represented by SEQ ID NO: 01;
    each antibody-displayed phage comprises proteins containing a phagemid vector in the inside thereof;
    each antibody-displayed phage comprises an antibody fragment on the external surface thereof; and
    the phagemid vector has a gene sequence coding for the antibody fragment;
    (b) heating the support to the temperature of not less than 37 degrees Celsius and not more than 70 degrees Celsius, so as to release a portion of the antibody-displayed phages from the support and so as to leave the other antibody-displayed phages on the support selectively;
    (c) collecting the other antibody-displayed phages which has been left on the support selectively in the step (b) so as to obtain the heat-stable antibody-displayed phage;
    (d) bringing a cell into contact with the heat-stable antibody-displayed phages collected in the step (c) to produce an infected cell; and
    (e) incubating the infected cell produced in the step (d) to acquire the heat-stable antibody fragment.

6. A heat-stable peptide consisting of the amino acid sequence represented by SEQ ID NO: 01.

7. The heat-stable peptide according to claim 6, wherein the peptide is stable even when the peptide is heated to 70 degrees Celsius.

* * * * *